United States Patent
Iakovlev et al.

(10) Patent No.: US 11,306,113 B2
(45) Date of Patent: Apr. 19, 2022

(54) PROCESS FOR THE PRODUCTION OF CELLULOSE, LIGNOCELLULOSIC SUGARS, LIGNOSULFONATE, AND ETHANOL

(71) Applicant: American Process International LLC, Atlanta, GA (US)

(72) Inventors: Mikhail Iakovlev, Atlanta, GA (US); Theodora Retsina, Atlanta, GA (US); Adriaan van Heiningen, Orono, ME (US); Myrto Papaioannou, Athens (GR); Eleni Natsi, Athens (GR)

(73) Assignee: American Process International LLC, Atlanta, GA (US)

( * ) Notice: Subject to any disclaimer, the term of this patent is extended or adjusted under 35 U.S.C. 154(b) by 0 days.

(21) Appl. No.: 16/875,241

(22) Filed: May 15, 2020

(65) Prior Publication Data
US 2021/0139519 A1    May 13, 2021

Related U.S. Application Data

(60) Provisional application No. 62/934,601, filed on Nov. 13, 2019.

(51) Int. Cl.
  *C07G 1/00* (2011.01)
  *C08B 1/00* (2006.01)
  (Continued)

(52) U.S. Cl.
  CPC ............ *C07G 1/00* (2013.01); *C08B 1/003* (2013.01); *C08L 97/02* (2013.01); *D21C 3/06* (2013.01)

(58) Field of Classification Search
  CPC .......................................................... D21C 3/06
  See application file for complete search history.

(56) References Cited

U.S. PATENT DOCUMENTS

| 1,856,567 A | 5/1932 | Theodor et al. |
| 2,060,068 A | 11/1936 | Groombridge |
| (Continued) | | |

FOREIGN PATENT DOCUMENTS

| EP | 2376642 A2 | 10/2011 |
| EP | 2358890 B1 | 3/2013 |
| (Continued) | | |

OTHER PUBLICATIONS

Wells et al., "Rapid Sulfite Pulping in Concentrated Sulfur Dioxide Solutions," Tappi, 52(11): 2136-2140, Nov. 1969.
(Continued)

*Primary Examiner* — Liam J Heincer
(74) *Attorney, Agent, or Firm* — Haukaas Fortius PLLC; Michael H. Haukaas

(57) ABSTRACT

A process for the production of cellulose, lignocellulosic sugars, lignosulfonate, and ethanol from lignocellulosic biomass. The process comprises steaming, pretreatment, chemical recovery, saccharification, and optionally fermentation. The pretreatment conditions use only sulfur dioxide and water, simultaneously resulting in high glucan conversion to glucose at low enzyme charges, high recovery of hemicellulose-derived monomeric sugars, high lignosulfonate yield, and the absence of lignin precipitates. High-yield production of ethanol through fermentation can be obtained using this process.

25 Claims, 8 Drawing Sheets

(51) Int. Cl.
*C08L 97/02* (2006.01)
*D21C 3/06* (2006.01)

(56) References Cited

U.S. PATENT DOCUMENTS

| | | | |
|---|---|---|---|
| 3,523,060 A * | 8/1970 | Walker, Jr. | D21C 3/06 |
| | | | 162/76 |
| 3,525,667 A * | 8/1970 | Avon | D21C 3/06 |
| | | | 162/62 |
| 3,585,104 A | 6/1971 | Kleinert | |
| 4,100,016 A | 7/1978 | Diebold et al. | |
| 4,211,605 A * | 7/1980 | Saxton | D21B 1/021 |
| | | | 162/64 |
| 4,764,596 A | 8/1988 | Lora et al. | |
| 7,754,457 B2 | 7/2010 | Foody et al. | |
| 8,003,352 B2 | 8/2011 | Foody et al. | |
| 8,030,039 B1 | 10/2011 | Retsina et al. | |
| 8,038,842 B2 | 10/2011 | Retsina et al. | |
| 8,216,809 B2 | 7/2012 | Diner et al. | |
| 8,247,203 B2 | 8/2012 | Foody et al. | |
| 8,268,125 B2 | 9/2012 | Retsina et al. | |
| 8,304,213 B2 | 11/2012 | Diner et al. | |
| 8,585,863 B2 | 11/2013 | Retsina et al. | |
| 8,834,633 B2 | 9/2014 | Van Der Meulen et al. | |
| 8,864,941 B2 | 10/2014 | Retsina et al. | |
| 8,946,491 B2 | 2/2015 | Radtke et al. | |
| 8,980,599 B2 | 3/2015 | Tolan et al. | |
| 9,068,236 B2 | 6/2015 | Heikkila et al. | |
| 9,139,857 B2 | 9/2015 | Retsina et al. | |
| 9,193,982 B2 | 11/2015 | Sjoede et al. | |
| 9,322,072 B2 | 4/2016 | Retsina et al. | |
| 9,434,961 B2 | 9/2016 | Dottori et al. | |
| 9,453,249 B2 | 9/2016 | Retsina et al. | |
| 9,528,129 B2 | 12/2016 | Van Der Meulen et al. | |
| 9,574,212 B2 | 2/2017 | Foody et al. | |
| 9,624,436 B2 | 4/2017 | Hamilton et al. | |
| 9,631,057 B2 | 4/2017 | Realff et al. | |
| 9,631,316 B2 | 4/2017 | Retsina et al. | |
| 10,344,303 B2 | 7/2019 | Retsina et al. | |
| 10,421,667 B2 | 9/2019 | Foody et al. | |
| 2002/0192774 A1* | 12/2002 | Ahring | C12P 7/10 |
| | | | 435/162 |
| 2007/0254348 A1 | 11/2007 | Retsina et al. | |
| 2010/0268000 A1* | 10/2010 | Parekh | C12P 7/065 |
| | | | 568/840 |
| 2011/0165643 A1 | 7/2011 | Retsina et al. | |
| 2011/0201084 A1 | 8/2011 | Wyman et al. | |
| 2011/0312033 A1* | 12/2011 | Gao | C12P 7/10 |
| | | | 435/72 |
| 2012/0006320 A1 | 1/2012 | Nguyen | |
| 2012/0202253 A1 | 8/2012 | Retsina et al. | |
| 2013/0071903 A1* | 3/2013 | Rowland | C08L 97/02 |
| | | | 435/162 |
| 2013/0143289 A1* | 6/2013 | Van Der Meulen | D21C 3/02 |
| | | | 435/145 |
| 2013/0274456 A1* | 10/2013 | Parekh | C13K 1/02 |
| | | | 536/1.11 |
| 2014/0154756 A1* | 6/2014 | Nelson | D21C 11/0007 |
| | | | 435/135 |
| 2014/0170713 A1* | 6/2014 | Retsina | C13K 1/02 |
| | | | 435/99 |
| 2014/0186898 A1* | 7/2014 | Retsina | C12P 19/02 |
| | | | 435/99 |
| 2014/0186899 A1* | 7/2014 | Retsina | C12P 19/02 |
| | | | 435/99 |
| 2014/0186901 A1* | 7/2014 | Retsina | D21C 3/20 |
| | | | 435/105 |
| 2015/0225756 A1 | 8/2015 | Retsina et al. | |
| 2015/0232703 A1* | 8/2015 | Nelson | C09D 197/005 |
| | | | 435/99 |
| 2015/0233057 A1* | 8/2015 | Tunc | D21C 11/12 |
| | | | 162/16 |
| 2015/0246978 A1* | 9/2015 | Szczepanik | C08B 37/0003 |
| | | | 435/105 |
| 2015/0354017 A1* | 12/2015 | Wang | C13K 1/04 |
| | | | 127/48 |
| 2016/0060667 A1* | 3/2016 | Monclin | C12P 19/02 |
| | | | 435/99 |
| 2016/0222586 A1 | 8/2016 | Retsina et al. | |
| 2016/0273163 A1 | 9/2016 | Gong et al. | |
| 2016/0312249 A1* | 10/2016 | Foody | C12P 7/14 |
| 2017/0002387 A1* | 1/2017 | Retsina | C08H 8/00 |
| 2017/0183698 A1* | 6/2017 | Noordam | D21C 3/263 |
| 2017/0342443 A1* | 11/2017 | Smits | C12N 1/14 |
| 2017/0369957 A1* | 12/2017 | Jansen | C13K 11/00 |
| 2018/0037863 A1* | 2/2018 | Foody | C12Y 302/01004 |
| 2018/0037915 A1* | 2/2018 | Foody | D21C 1/04 |
| 2018/0251941 A1* | 9/2018 | Nelson | D21C 3/06 |
| 2018/0355303 A1 | 12/2018 | Rowland et al. | |
| 2018/0363017 A1 | 12/2018 | Tolan et al. | |
| 2019/0106464 A1 | 4/2019 | Oeser et al. | |
| 2019/0106718 A1 | 4/2019 | Foody et al. | |
| 2019/0194697 A1* | 6/2019 | Dechman | C10L 1/02 |
| 2019/0376236 A1* | 12/2019 | Sixta | D21C 11/00 |
| 2020/0056213 A1* | 2/2020 | Retsina | C12P 7/10 |

FOREIGN PATENT DOCUMENTS

| | | |
|---|---|---|
| EP | 2588664 B1 | 1/2017 |
| WO | 2007146245 A2 | 12/2007 |
| WO | 2011106879 A1 | 9/2011 |
| WO | 2014099186 A1 | 6/2014 |
| WO | 2014106220 A1 | 7/2014 |
| WO | 2014106221 A1 | 7/2014 |
| WO | 2014106222 A2 | 7/2014 |
| WO | 2014203271 A3 | 2/2015 |
| WO | 2015200584 A1 | 12/2015 |
| WO | 2015200868 A1 | 12/2015 |
| WO | 2016029069 A1 | 2/2016 |
| WO | 2016144881 A1 | 9/2016 |
| WO | 2019090413 A1 | 5/2019 |
| WO | 2019090414 A1 | 5/2019 |
| WO | 2019191828 A1 | 10/2019 |

OTHER PUBLICATIONS

Westmoreland et al., "Sulfur Dioxide-Ethanol-Water Pulping of Hardwoods," Chem Eng Comm., 104:101-115, Jan. 1991.

Yamamoto et al., "The Effect of Chemical and Physical Characteristics of Spruce SEW Pulps on Enzymatic Hydrolysis," Cellulose, 21:3395-3407, Aug. 2014.

Yu et al., "The Effect of Delignification of Forest Biomass on Enzymatic Hydrolysis," Bioresour Technol., 102(19):9083-9089, Oct. 2011.

Zhou et al., "Bioconversion of Beetle-Killed Lodgepole Pine Using SPORL: Process Scale-up Design, Lignin Coproduct, and High Solids Fermentation without Detoxification," Ind. Eng. Chem. Res., 52(45):16057-16065, Oct. 2013.

Zhu et al., "Ethanol Production From SPORL-Pretreated Lodgepole Pine: Preliminary Evaluation of Mass Balance and Process Energy Efficiency," Appl Microbiol Biotechnol., 86(5):1355-1365, May 2010.

Zhu et al., "Using Sulfite Chemistry for Robust Bioconversion of Douglas-Fir Forest Residue to Bioethanol at High Titer and Lignosulfonate: A Pilot-Scale Evaluation," Bioresour Technol., 179:390-397, Mar. 2015.

Achyuthan et al., "Supramolecular Self-Assembled Chaos: Polyphenolic Lignin's Barrier to Cost-Effective Lignocellulosic Biofuels," Molecules, 15(12):8641-8688, Nov. 2010.

Aro et al., "Production and Application of Lignosulfonates and Sulfonated Lignin," ChemSusChemr., 10(9):1861-1877, Mar. 2017.

Aziz et al., "Organosolv Pulping—A Review," Tappi J (USA), 72(3):169-175, Mar. 1989.

Buzás et al., "Influence of pH on the Growth and Ethanol Production of Free and Immobilized *Saccharomyces cerevisiae* Cells," Biotechnol. Bioeng., 34:882-884, Sep. 1989.

Carvalheiro et al., "Hemicellulose Biorefineries: A Review on Biomass Pretreatments," J Scient Ind Res., 67(11):849-864, Nov. 2008.

(56) References Cited

OTHER PUBLICATIONS

Chen et al., "Pulp Characteristics and Mill Economics for a Conceptual So2-ethanol-Water Mill," AGRIS, 1990 Pulping Conference, pp. 663-672, 1992.

Chum et al., "Pretreatment-Catalyst Effects and the Combined Severity Parameter," Appl Biochem Biotechnol., 24-25(1):1-14, Mar. 1990.

Del Rio et al, "The Effect of Varying Organosolv Pretreatment Chemicals on the Physicochemical Properties and Cellulolytic Hydrolysis of Mountain Pine Beetle-Killed Lodgepole Pine," Appl Biochem Biotechnol., 161(1-8):1-21, May 2010.

Eliashberg et al., "Wood Delignification with So2 Solutions Free from Bisulphite," Trudy Leningrad. Lesotekh. Akad.,1960, 11pgs.

Ewanick et al., "Acid-Catalyzed Steam Pretreatment of Lodgepole Pine and Subsequent Enzymatic Hydrolysis and Fermentation to Ethanol," Biotechnol Bioeng., 98(4):737-746, Nov. 2007.

Fatehi et al., "Chap. 2: Extraction of Technical Lignins from Pulping Spent Liquors, Challenges and Opportunities," Production of Biofuels and Chemicals from Lignin, Springer, 1st ed., 2016 edition, pp. 35-54, Oct. 2016.

Fernando et al., "Lignin Recovery from Spent Liquors from Ethanol-Water Fractionation of Sugar Cane Bagasse," Cellulose Chem Technol., 44(9):311-318, Sep. 2010.

Galbe et al., "A Review of the Production of Ethanol From Softwood," Appl Microbiol Biotechnol., 59(6):618-628, Sep. 2002.

Gütsch et al., "Purification of Eucalyptus Globulus Water Prehydrolyzates Using the HiTAC Process (High-Temperature Adsorption on Activated Charcoal)," Holzforschung, 65(4):511-518, Apr. 2011.

Holtzapple et al., "The Effect of Organosolv Pretreatment on the Enzymatic Hydrolysis of Poplar," Biotechnol. Bioeng., 26:670-676, Jul. 1984.

Kleinert, "Organosolv Pulping with Aqueous Alcohol," Tappi J., 57(8):99-102, Aug. 1974.

Kumar et al. "The Lignin Present in Steam Pretreated Softwood Binds Enzymes and Limits Cellulose Accessibility," Bioresour Technol., 103(1):201-208, Jan. 2012.

Lan et al., "High Titer Ethanol Production From SPORL-Pretreated Lodgepole Pine by Simultaneous Enzymatic Saccharification and Combined Fermentation," Bioresour Technol., 127:291-297, Jan. 2013.

Larsson, et al., "The Generation of Fermentation Inhibitors During Dilute Acid Hydrolysis of Softwood," Enzyme Microb Tech., 24(3-4):151-159, Feb.-Mar. 1999.

Morales et al., "Effects of Residual Lignin and Heteropolysaccharides on the Bioconversion of Softwood Lignocellulose Nanofibrils Obtained by SO2-Ethanol-Water Fractionation," Bioresour Technol., 161:55-62, Jun. 2014.

Nakagame et al., "The Effect of Isolated Lignins, Obtained From a Range of Pretreated Lignocellulosic Substrates, on Enzymatic Hydrolysis," Biotechnol Bioeng., 105(5):871-879, Apr. 2010.

Nitsos et al., "Isolation and Characterization of Organosolv and Alkaline Lignins From Hardwood and Softwood Biomass," ACS Sustainable Chem. Eng., 4(10):5181-5193, Sep. 2016.

Olsson et al., "Fermentative Performance of Bacteria and Yeasts in Lignocellulose Hydrolysates," Process Biochem., 28(4):249-257, Jan. 1993.

Pan et al., "Biorefining of Softwoods Using Ethanol Organosolv Pulping: Preliminary Evaluation of Process Streams for Manufacture of Fuel-Grade Ethanol and Co-Products," Biotechnol Bioeng., 90(4):473-481, May 2005.

Pan et al., "Pretreatment of Lodgepole Pine Killed by Mountain Pine Beetle Using the Ethanol Organosolv Process: Fractionation and Process Optimization," Ind Eng Chem Res.,46(8):2609-2617, Mar. 2007.

Perez et al., "Effect of Process Variables on Liquid Hot Water Pretreatment of Wheat Straw for Bioconversion to Fuel-Ethanol in a Batch Reactor," J Chem Technol Biotechnol., 82(10):929-938 Oct. 2007.

Pfister et al., "The Formation of Monosaccharides and Aldonic and Uronic Acids During Sulphite Cooking," Paperi ja Puu (Paper and Wood), 59(11):711-720, 1977.

Primakov, "Delignification of Various Wood Species with So2 Aqueous-Alcohol Solutions," Proceedings of the All-Union Research and Development Institute of Pulp and Paper Industry, 47, 1961, 8pgs.

Primakov, "Larch Wood Delignification with So2 Aqueous-Alcohol Solutions," Proceedings of the All-Union Research and Development Institute of Pulp and Paper Industry, 46, 1961, 36pgs.

Primakov, "Optimization of Wood Pulping with So2 Aqueous-Alcohol Solutions," Wood Chemistry, 2:44-47, 1988.

Puumala, "Organosolv Pulping and a Preliminary Vapor-Liquid Equilibrium Study of a Sulfur Dioxide, Ethanol, Water System," A Thesis, Michigan Technological University, May 1991, pp. 1-67.

Pylkkänen, "Characterization of the Ethanol-So2 Pulping and a Preliminary Chemical Recovery Process Design," A Thesis, Lappeenranta-Lahti University of Technology LUT, Jun. 1992, pp. 1-141.

Rahikainen et al., Inhibition of Enzymatic Hydrolysis by Residual Lignins From Softwood—Study of Enzyme Binding and Inactivation on Lignin-Rich Surface, Biotechnol Bioeng., 108(12):2823-2834, Dec. 2011.

Saddler, et al., "Enzymatic Hydrolysis of Cellulose and Various Pretreated Wood Fractions," Biotechnol Bioeng., 24(6):1389-1402, Jun. 1982.

Sannigrahi et al., "Fundamentals of Biomass Pretreatment by Fractionation," 2013 JohnWiley & Sons, Ltd., pp. 201-222, Apr. 2013.

Schulze et al., "Advanced Process for Precipitation of Lignin From Ethanol Organosolv Spent Liquors," Bioresour Technol., 199:128-134, Jan. 2016.

Sixta, H., "Handbook of Pulp," Wiley-VCH, pp. 421.424, Mar. 2006.

Sjöström, "Wood Chemistry: Fundamentals and Applications," Academic Press; 2 edition, Chap. 7, Secs. 7.2-7.3, Jul. 1981.

Sklavounos et al., "Comparison of Two Conditioning Scheme S for Detoxifying SO 2 Ethanol Water Hydrolysate From Lignocellulosics for ABE Fermentation," Nord Pulp Pap Res J., 29(3):370-382, Mar. 2014.

Sklavounos et al., "Conditioning of SO2-Ethanol-Water Spent Liquor From Spruce for the Production of Chemicals by ABE Fermentation," Holzforschung, 65:551-558, Jun. 2011.

Sklavounos et al., "Oil Palm Empty Fruit Bunch to Biofuels and Chemicals via SO2-Ethanol-Water Fractionation and ABE Fermentation," Bioresource Technol., 147:102-109, Nov. 2013.

Sklavounos et al., "Study on Conditioning of SO2-Ethanol-Water Spent Liquor from Spruce Chips/Softwood Biomass for ABE Fermentation," Ind. Eng. Chem. Res., 52(11):4351-4359, Feb. 2013.

Söderström et al., "Effect of Washing on Yield in One- and Two-Step Steam Pretreatment of Softwood for Production of Ethanol," Biotechnol Prog., 20(3)744-749, May-Jun. 2004.

Stanciu et al., "Research Concerning Formation, Characterization and Recovery of Lignin Polymeric Deposits in order to Get Some Lignin-phenol-formaldehyde Resins," Materiale Plastice, 45(3):232-235, Sep. 2008.

Stenberg et al., "Optimisation of Steam Pretreatment of SO2-Impregnated Mixed Softwoods for Ethanol Production," J Chem Technol Biotechnol., 71:299-308, Jan. 1998.

Tian et al., "Comparisons of SPORL and Dilute Acid Pretreatments for Sugar and Ethanol Productions From Aspen," Biotechnol Prog., 27(2):419-427, Mar.-Apr. 2011.

Van Heiningen et al., "Reactions of Ethanol with Xylan and Lignin in Acid Catalyzed Organolv Pulping; Implications for Ethanol Recovery and Process Selection," 15th European Workshop on Lignocellulosics and Pulp, Jun. 2018, 4pgs.

Van Heiningen et al., "Reactions of Ethanol with Xylan and Lignin in Acid Catalyzed Organolv Pulping; Implications for Ethanol Recovery and Process Selection," Final Paper, 15th European Workshop on Lignocellulosics and Pulp, Jun. 2018, 4pgs.

Várnai et al., "Restriction of the Enzymatic Hydrolysis of Steam-Pretreated Spruce by Lignin and Hemicellulose," Enzyme Microb Tech., 46(3-4):185-193, Mar. 2010.

(56) References Cited

OTHER PUBLICATIONS

Wang et al., "Ethanol Production From Poplar Wood Through Enzymatic Saccharification and Fermentation by Dilute Acid and SPORL Pretreatments," Fuel, 95:606-614, May 2012.
Extended Search Report of the European Patent Office dated Oct. 7, 2020 in EP Application No. 20174836.5; 10pgs.
Yamamoto et al., "Total Mass Balances of SO2-ethanol-water (SEW) Fractionation of Forest Biomass," Holzforschung, 65:559-565, Jun. 2011.
International Search Report and Written Opinion of the ISA/EP in PCT/US2020/060494, dated Feb. 11, 2021; 11pgs.
International Search Report and Written Opinion of the ISA/EP in PCT/US2020/060543, dated Feb. 8, 2021; 21pgs.
NGUYEN et al., "Two-Stage Dilute-Acid Pretreatment of Softwoods," Appl. Biochem. Biotechnol., 84-86:561-576, Spring 2000.
Rydholm, Pulping Processes, Interscience Publishers, 1965, p. 456.
Shi et al., "Degradation Kinetics of Monosaccharides in Hydrochloric, Sulfuric, and Sulfurous Acid," Bioresources, 7(3):4085-4097, Aug. 2012.
Shi et al., "Existence of the Sugar-Bisulfite Adducts and Its Inhibiting Effect on Degradation of Monosaccharide in Acid System," Appl Biochem Biotechnol., 172:1612-1622, Feb. 2014.
Tengborg et al., "Comparison of S02 and H2S04 Impregnation of Softwood Prior to Steam Pretreatment on Ethanol Production," Appl. Biochem. Biotechnol.,. 70-72(3):3-15 Mar. 1998.

\* cited by examiner c d

PROCESS FOR THE PRODUCTION OF CELLULOSE, LIGNOCELLULOSIC SUGARS, LIGNOSULFONATE, AND ETHANOL

RELATED APPLICATIONS

This application claims priority under 35 U.S.C. § 119(e) to U.S. Provisional Patent Application No. 62/934,601 filed Nov. 13, 2019, which is incorporated herein by reference.

FIELD OF THE INVENTION

The invention generally relates to pretreatment processes for converting lignocellulosic biomass to lignin, cellulose, fermentable sugars, and ethanol.

BACKGROUND OF THE INVENTION

Commercial sulfite and Kraft pulping processes have been practiced since the end of $19^{th}$ century/beginning of $20^{th}$ century. The Kraft process utilizes alkaline chemistry (pH 13-14) at temperatures of about 140-175° C. where the cooking liquor is an aqueous solution of sodium hydroxide and sodium sulfide. The sulfite process is performed across a wide pH range of about 1 to about 13 at temperatures of about 125-180° C. where the cooking liquor is an aqueous solution of sulfur dioxide ($SO_2$) and salts of sulfurous acid, i.e. sulfites and hydrogen sulfites. Magnesium, calcium, sodium, and ammonium are used as bases (Sjöström, 1981). These processes aim at separation of cellulose pulp, while other biomass components, primarily lignin and hemicelluloses, are degraded to a large extent.

The Kraft process substantially alters the lignin structure by introducing sulfide bridges, removing methoxyl groups, and changing lignin molecular weight, while hemicellulosic sugars heavily degrade in the alkali, resulting in a complex mixture of lactic and other hydroxy carboxylic acids. Acid sulfite and bisulfite processes, the two most common varieties of sulfite pulping, utilize hydrogen sulfite anions as the delignification chemical resulting in lignin sulfonation to lignosulfonic acids and sugar oxidation to aldonic acids. A substantial portion of sugars is lost in both processes (>70% in Kraft; >20-30% in sulfite, Pfister and Sjöström 1977).

Both processes have rather inefficient and/or expensive chemical recovery systems. In the sulfite process, inorganic side reactions take place leading to sulfur loss as thiosulfate, polythionates, sulfate, and elemental sulfur (Sixta et al., 2006). In addition, the acid sulfite process is very sensitive to raw material selection, particularly the raw material species, particle size, and shape. Many types of woody biomass, including pine, are not suitable for the acid sulfite process. Moreover, a long impregnation phase (a few hours) at low temperatures (below about 100-110° C.) is required in sulfite cooking for the efficient transport of chemicals into the cell wall structure. Without such slow impregnation, lignin condensation and reprecipitation on the fibers is substantial, and 'a black cook' is observed.

Sulfur Dioxide-Based Pretreatment Technologies. The patent EP 2376642 (Sjoede) "LIGNOCELLULOSIC BIOMASS CONVERSION BY SULFITE PRETREATMENT" describes sulfite pretreatment to convert biomass to cellulose, fermentable sugars, lignosulfonate and ethanol. The sulfite pretreatment is similar to the acid sulfite process described above.

The SPORL process is somewhat similar to the sulfite process where, in addition to sulfur dioxide and salts of sulfurous acids, it occasionally utilizes sulfuric acid, it does not practice impregnation, and it does not aim at a high cellulose content in pulp. Temperatures between 130 and 180° C. are used. The process purportedly performs better than dilute acid pretreatment in terms of cellulose enzymatic digestibility (Tian et al., 2011, Wang et al., 2012). However, the presence of hydrogen sulfite anions and acidity lead to sugar degradation. The total monomeric sugar recovery was reported at about 520 kg per BD tonne of Douglas Fir (Zhu et al., 2015). Recovery of a complex mixture of hydrogen sulfites, sulfites, and sulfates presents a hardly solvable challenge.

In both sulfite and SPORL processes, a base is required to neutralize the formed lignosulfonic acid (a very strong acid; pKa~1). Without the neutralization, high acidity within the cell wall will result in lignin condensation and reprecipitation on the fibers as well as on the equipment. On the other hand, it is a challenge to produce pulps with low lignin content using only $SO_2$ and water, i.e., without any base (Sjöström, 1981).

The AVAP® process (Retsina: U.S. Pat. No. 8,038,842 "METHOD FOR VAPOR PHASE PULPING WITH ALCOHOL, SULFUR DIOXIDE AND AMMONIA", U.S. Pat. No. 8,268,125 "METHOD FOR VAPOR PHASE PULPING WITH ALCOHOL AND SULFUR DIOXIDE") utilizes sulfur dioxide, an organic solvent, and water at temperatures of about 135-160° C. The organic solvent replaces the base of the sulfite process as an acidity moderator. The AVAP® process allows for efficient delignification, high cellulose enzymatic digestibility and low sugar losses. However, it employs organic solvents typically at about 40-60% of the liquor or about 1.2-1.8 tonnes per BD tonne biomass. The solvent requires safe handling as well as efficient and quantitative recovery, which includes efficient pulp washing and additional unit operations, for instance, steam stripping and heat treatment of the hemicellulose pulping liquor. The high concentration solvent processing equipment should therefore be explosion-proof.

Steam explosion, hot water treatment and dilute acid pretreatment processes (150-220° C.) are widely covered in academic literature despite the obvious disadvantages of high sugar degradation, lignin condensation, low enzymatic digestibility of cellulose, formation of sticky lignin precipitates, non-applicability to softwoods, and in case of dilute acid, acid recovery challenges. For example, Perez et al. (2008) reported at least 47% hemicellulose sugar loss in optimized hot water pretreatment of wheat straw. In another report, dilute sulfuric acid pretreatment of pine resulted in only 43% glucan-to-glucose conversion at enzyme dosage of about 22 FPU/g glucan. Total monomeric sugar recovery was only 248 kg per BD tonne biomass feed (Zhu et al., 2010).

Low $SO_2$ pretreatment processes have been extensively discussed in literature. They are referred to as $SO_2$-catalyzed steam explosion (Soderstrom et al., 2004, Stenberg et al., 1998, Galbe and Zacchi, 2002, Ewanick et al., 2007) or heat treatment of biomass impregnated with gaseous sulfur dioxide (van der Meulen: EP 2516660, U.S. Pat. Nos. 8,834,633, 9,528,129). In these processes, the $SO_2$ concentration in the liquid is generally below 3-6%, the temperature is about 150-215° C., and the pH of the liquors after pretreatment is generally 2-3, indicating that the residual concentration of sulfur dioxide is low. Low $SO_2$ pretreatments behave similarly to dilute acid pretreatments as most $SO_2$ is consumed to form strong lignosulfonic acid, and thus lignin condensation and reprecipitation on fibers are observed and sticky precipitates are expected. A high residual lignin content of the cellulosic fibers results in lower than optimal enzymatic digestibility of cellulose, with only 60-70% glucan-to-glucose conversion at enzyme dosages of higher or substantially higher than 20 FPU/g glucan. Total monomeric sugar yields of only about 470-520 kg per BD tonne biomass feed or below have been reported (Soderstrom et al., 2004, Stenberg et al., 1998, Galbe and Zacchi, 2002, Ewanick et al., 2007). These values are higher than those of the dilute acid pretreatment.

Sulfur dioxide pretreatments with water presoaking/dewatering of biomass or wet oxidation of biomass prior to pretreatment have been described in U.S. Pat. No. 9,574,212 (Foody "PROCESS COMPRISING SULFUR DIOXIDE AND/OR SULFUROUS ACID PRETREATMENT AND ENZYMATIC HYDROLYSIS") and U.S. Pat. No. 10,421,667 (Foody "PROCESS FOR TREATING LIGNOCELLULOSIC FEEDSTOCK COMPRISING WET OXIDATION"). These processes require additional unit operations increasing the capital and operational costs.

Recovery of chemicals is a decisive factor for the economic viability of a pretreatment process. Non-volatile inorganic acids (dilute acid, SPORL), alkalis, and salts (sulfite, SPORL) cannot be efficiently recovered, while sulfur dioxide is easy to recover, for example, by flashing. Recovery of the base is a major drawback of most base-utilizing processes. Alkaline processes, including Kraft pulping, are less attractive because of the expensive and complex recovery of the alkali.

Enzymatic digestibility of cellulose is another key factor for an economical process. Many studies have demonstrated strong negative correlation between cellulose enzymatic digestibility and residual lignin and hemicelluloses content (Varnai et al., 2010, Yamamoto et al., 2014, Morales et al., 2014). Both accessibility of cellulose to enzymes and non-productive enzyme adsorption on lignin are responsible for this correlation (Rahikainen et al., 2011, Kumar et al., 2012). In particular, these factors are relevant to softwoods (gymnosperms). Softwoods are the most recalcitrant type of biomass and show inferior enzymatic digestibility compared to hardwoods and annual/perennial plants (angiosperms) (Yu et al. 2011, Nakagame et al. 2010, Achyuthan et al. 2010). Thus, maximal dissolution of non-cellulose components is desirable as well. Most acidic pretreatments result in extensive dissolution of hemicelluloses but only partial removal of lignin. Therefore, the enzymatic digestibility is still limited due to remaining blockage by lignin and residual hemicelluloses tightly bound to the cellulose microfibrils.

The problem of lignin sticky precipitates is often overlooked in short term laboratory tests, but it becomes apparent after several days of continuous industrial operation. In conventional acidic processes (steam explosion, hot water, dilute acid, etc.), sugars degrade to furfural, HMF, humins, levulinic acid, and formic acid, while dissolved lignin condenses by reacting with other lignin units and with sugar degradation products. The condensed lignin is a sticky substance that reprecipitates on cellulose surface and plugs equipment. No solution is presently available for this problem (Stanciu and Ciurea, 2008, Gutsch and Sixta, 2011). On the other hand, alkaline based processes, like Kraft or AFEX, which can keep the lignin soluble, often destroy a high percentage of the hemicelluloses and burden the process with the high cost of recovering the base used.

It is also a common knowledge that fiber explosion (i.e., rapid decrease in pressure leading to instantaneous evaporation of liquid within the fiber structure) after pretreatment results in increased enzymatic digestibility of cellulose, presumably due to the disruption of fiber cell wall structure during the explosive decompression and thus improved enzyme accessibility to cellulose surface.

Thus, current pretreatment processes do not achieve simultaneous high-yield production of cellulose or cellulose-derived fermentable glucose and hemicellulose-derived fermentable monomeric sugars at a combined yield of higher than about 80% based on available polysaccharides in the biomass, in an economical manner without producing sticky lignin precipitates.

SUMMARY

The present disclosure describes a pretreatment process utilizing only sulfur dioxide and water for lignocellulosic biomass valorization resulting in simultaneously achieved high enzymatic digestibility of cellulose, high yield of hemicellulose-derived monomeric sugars and lignosulfonate, and absence of lignin precipitates. The process allows conversion of higher than 82%, higher than 86%, or higher than 90% of available saccharides to monosaccharides, and conversion of higher than 75%, higher than 80%, higher than 85%, or higher than 90% of available lignin to lignosulfonate. The process involves pretreatment with a pretreatment composition comprising a solution or mixture of sulfur dioxide and water at high sulfur dioxide concentrations and at relatively low temperatures (125-140° C.), followed by recovery of sulfur dioxide, producing (separately or mixed together) cellulose pulp, hemicellulose-derived monomeric sugars, and lignosulfonic acid or lignosulfonate. A high concentration of sulfur dioxide in a pretreatment composition is defined as 15-60 weight % sulfur dioxide in the composition based on the total weight of sulfur dioxide and water in the pretreatment composition.

In some embodiments, the cellulose is then subjected to saccharification. In various embodiments, the hemicellulose-derived monomeric sugars are subjected to fermentation conditions to produce ethanol, and in some embodiments, the hemicellulose-derived monomeric sugars are combined with the cellulose saccharification products, which are then subjected to fermentation conditions to produce ethanol.

Process 1.

In a first embodiment, referred to herein as Process 1, the invention provides a process for producing cellulose, lignocellulosic sugars, lignosulfonate, and ethanol, from lignocellulosic biomass comprising:

(a) contacting lignocellulosic biomass in a first container (e.g., a steaming bin) with steam, wherein the lignocellulosic biomass absorbs water from the steam, removing air and optionally turpentine and/or other extractives from the lignocellulosic biomass;

(b) contacting the steamed lignocellulosic biomass in the second container (e.g., a digester) with a pretreatment composition comprising sulfur dioxide and water at a temperature between about 125° C. and about 140° C. under pressure for 20-120 minutes to generate pretreated material;

wherein the pretreatment composition comprises 15-60 wt. % sulfur dioxide and 40-85 wt. % water based on the combined weight of sulfur dioxide and water (including water from the steamed lignocellulosic biomass), and the ratio of pretreatment composition to lignocellulosic biomass dry weight is from about 1 to about 10 kg/kg (including water from the steamed lignocellulosic biomass in the mass of the pretreatment composition);

thereby releasing and/or dissolving lignin and hemicellulose from the lignocellulosic biomass into the pretreatment composition and leaving a solid fraction that is mostly cellulose, defined as cellulose content of greater than 75%, greater than 80%, greater than 85%, or greater than 90%, by weight, based on the dry solid fraction, wherein the remaining mass includes residual lignin and residual hemicelluloses;

wherein 75-100% of the lignin from the lignocellulosic biomass is sulfonated to produce lignosulfonic acid (LS), and at least about 85% of the sugar moieties of the released hemicellulose from the lignocellulosic biomass are hydrolyzed to monosaccharide form (in other words, at least 85% of total hemicellulose-derived sugar moieties that are present in the pretreated material are in monosaccharide form);

(c) releasing pressure from the pretreated material, and recovering sulfur dioxide from gas released from the pretreated material as a result of releasing pressure, optionally retaining the dissolved material at elevated temperature to facilitate sulfur dioxide recovery;

(d) removing dissolved material from the cellulose by washing with water or by applying pressure to the cellulose to drain off the dissolved material, to provide washed cellulose or pressed cellulose, wherein the dissolved material comprises lignosulfonic acid (LS), lignin, hemicellulose oligomers, and monosaccharides, optionally retaining the dissolved material at elevated temperature to facilitate sulfur dioxide recovery;

(e) optionally adjusting pH of the washed cellulose stream from step (d) (e.g., to a pH of about 4.8 to about 5.8), and contacting it with a cellulase, a glucosidase, a hemicellulase, or a combination thereof, to produce glucose and release small amounts of insoluble lignin and hemicellulose-derived monosaccharides (where small amounts refer to less than about 4%, less than about 5%, less than about 6%, or less than 10%, by weight, of the washed cellulose stream); and (f) optionally neutralizing the glucose and the dissolved material to appropriate pH level (e.g., between about 5.5 and about 6.0) and subjecting the glucose, the dissolved material, or a combination thereof to fermentation to produce ethanol.

In some embodiments, one or more of water, phosphoric acid, hydrochloric acid, sulfuric acid, nitric acid, acetic acid, formic acid, oxalic acid, and process condensates are added to step (c), step (d), or both. Process condensates can include, for example, the condensate in step (ii) of recovering sulfur dioxide (see below).

Slurries or solutions of the process (e.g., the pulp slurry obtained after step (c) or the dissolved material removed in step (d), or both) are subjected to pH adjustment before the enzyme hydrolysis of step (e), before fermentation in step (f), or before both steps (e) and (f). The pH can be adjusted to a pH from about 4.5 to about 6 or from about 4.8 to about 5.8, or from about 5.0 to about 5.5. The pH adjustment can be carried out by the addition of aqueous solutions, slurries, or pure compounds of calcium oxide, calcium hydroxide, potassium hydroxide, sodium hydroxide, magnesium oxide, magnesium hydroxide, ammonium hydroxide, or a combination thereof.

In some embodiments, the pH of the slurries or solutions of the process can be temporarily increased, and then decreased, which aids the removal of enzyme and fermentation inhibitors, for example, any furfural, HMF, aromatics, sulfite, sulfate. For example, the pH can be adjusted to a pH from about 7 to about 11 (e.g., 7, 7.5, 8, 8.5, 9, 9.5, 10, 10.5, or 11) before the enzyme hydrolysis of step (e), before fermentation in step (f), or before both steps (e) and (f), followed by adjusting the pH to about 4.5 to about 6. The pH increase can be carried out by the addition of calcium oxide, calcium hydroxide, potassium hydroxide, sodium hydroxide, magnesium oxide, magnesium hydroxide, ammonium hydroxide, or combination thereof. The pH decrease can be carried out using phosphoric acid, hydrochloric acid, sulfuric acid, nitric acid, acetic acid, formic acid, oxalic acid, or a combination thereof.

Residual sulfur dioxide, hydrogen sulfites, and/or sulfites can be removed from process slurries or solutions, before enzyme hydrolysis in step (e), before fermentation in step (f), or before both steps (e) and (f), by adding one or more aqueous solutions comprising formaldehyde, acetaldehyde, or hydrogen peroxide.

The process can further comprise bleaching the washed pulp to produce cellulose that can be converted to nanocellulose and/or dissolving pulp, including but not limited to viscose, cellulose ethers, and cellulose esters.

Process 2.

In a second embodiment, referred to herein as Process 2, the invention provides a process for producing lignocellulosic sugars, lignosulfonate, and ethanol, from lignocellulosic biomass comprising:

(a) contacting lignocellulosic biomass in a first container (e.g., a steaming bin) with steam, wherein the lignocellulosic biomass absorbs water from the steam, removing air and optionally turpentine and/or other extractives from the lignocellulosic biomass;

(b) contacting the steamed lignocellulosic biomass in a second container (e.g., a digester) with a pretreatment composition comprising sulfur dioxide and water at a temperature between 125° C. and 140° C. under pressure for 20-120 minutes to generate pretreated material;

wherein the pretreatment composition comprises 15-60 wt. % sulfur dioxide and 40-85 wt. % water based on the combined weight of sulfur dioxide and water (including water from the steamed lignocellulosic biomass), and the ratio of pretreatment composition to lignocellulosic biomass dry weight is from about 1 to about 10 kg/kg (including water from the steamed lignocellulosic biomass in the mass of the pretreatment composition);

thereby releasing and/or dissolving lignin and hemicellulose from the lignocellulosic biomass into the pretreatment composition and leaving a solid fraction that is mostly cellulose, defined as cellulose content of greater than 75%, greater than 80%, greater than 85%, or greater than 90%, by weight, based on the dry solid fraction, wherein the remaining mass includes residual lignin and residual hemicelluloses;

wherein 75-100% of the lignin from the lignocellulosic biomass is sulfonated to produce lignosulfonic acid (LS), and at least about 85% of the sugar moieties of the released hemicellulose from the lignocellulosic biomass are hydrolyzed to monosaccharide form (in other words, at least 85% of total hemicellulose-derived sugar moieties that are present in the pretreated material are in monosaccharide form);

(c) releasing pressure from the pretreated material and recovering sulfur dioxide from gas released from the pretreated material as a result of releasing pressure, producing the first mixture, and optionally retaining the material at elevated temperature to facilitate sulfur dioxide recovery;

(d) neutralizing the first mixture to appropriate pH level for enzymatic hydrolysis, e.g. from about 4.5 to about 6;

(e) contacting the neutralized first mixture with a cellulase, a glucosidase, a hemicellulase, or a combination thereof, to provide a second mixture comprising glucose derived from cellulose and monosaccharides derived from hemicellulose as well as lignosulfonate (salt of lignosulfonic acid), lignin, and oligosaccharides; and (f) optionally adjusting pH of the second mixture (e.g., between about 5.5 and about 6.0), and subjecting the second mixture to fermentation to produce ethanol.

In some embodiments, one or more of water, phosphoric acid, hydrochloric acid, sulfuric acid, nitric acid, acetic acid, formic acid, oxalic acid, process condensates can be added to step (c).

Slurries or solutions of the process (e.g., the pulp slurry obtained after step (c) or the neutralized material after step (d), or both) are subjected to pH adjustment before the enzyme hydrolysis of step (e), before fermentation in step (f), or before both steps (e) and (f). The pH can be adjusted to a pH from about 4.5 to about 6 or from about 4.8 to about 5.8, or from about 5.0 to about 5.5. The pH adjustment can be carried out by the addition of aqueous solutions, slurries, or pure compounds of calcium oxide, calcium hydroxide, potassium hydroxide, sodium hydroxide, magnesium oxide, magnesium hydroxide, ammonium hydroxide, or a combination thereof.

In some embodiments, the pH of the slurries or solutions of the process can be temporarily increased, and then decreased, which aids the removal of enzyme and fermentation inhibitors, for example, any furfural, HMF, aromatics, sulfite, sulfate. For example, the pH of the first mixture after step (c), the second mixture after step (e), or both, can be adjusted to a pH from about 7 to about 11 (e.g., 7, 7.5, 8, 8.5, 9, 9.5, 10, 10.5, or 11) before the enzyme hydrolysis of step (e), before fermentation in step (f), or before both steps (e) and (f), followed by adjusting the pH to about 4.5 to about 6. The pH increase can be carried out by the addition of calcium oxide, calcium hydroxide, potassium hydroxide, sodium hydroxide, magnesium oxide, magnesium hydroxide, ammonium hydroxide, or combination thereof. The pH decrease can be carried out using phosphoric acid, hydrochloric acid, sulfuric acid, nitric acid, acetic acid, formic acid, oxalic acid, or a combination thereof.

Residual sulfur dioxide, hydrogen sulfites, and/or sulfites can be removed from the first mixture after step (c), the second mixture after step (e), or from both, by adding one or more aqueous solutions comprising formaldehyde, acetaldehyde, or hydrogen peroxide.

Process 1 and Process 2.

In each of the processes, recovering sulfur dioxide in the process can include:

(i) releasing gas comprising sulfur dioxide from the pretreated material at elevated temperature and optionally lower pressure, wherein the gas further may contain water vapor, non-condensable gases (e.g. carbon dioxide), and organic volatiles (e.g., acetic acid, methanol, methyl acetate, and furfural);

(ii) condensing any water vapor and organic volatiles to provide a gas comprising sulfur dioxide and optionally comprising non-condensable gases, and a liquid comprising water and organic volatiles;

(iii) liquefying sulfur dioxide gas by pressure change (e.g., a pressure increase) and/or temperature reduction of the gas to provide liquid sulfur dioxide, and optionally releasing any non-condensable gases; and (iv) introducing the liquid sulfur dioxide to a container for contacting steamed lignocellulosic biomass with a pretreatment composition, optionally by pumping.

The sulfur dioxide gas can be purified by removing traces of other compounds, including but not limited to, water vapor and other volatiles (e.g., acetic acid, methanol, methyl acetate, and furfural).

In some embodiments, the liquid sulfur dioxide is stored as liquid sulfur dioxide in a separate container before being reused in the pretreatment composition in step (b) of the process.

In some embodiments, the pretreated material is retained at elevated temperature after step (c), after step (d), or after steps (c) and (d), to facilitate sulfur dioxide recovery.

In some embodiments, the step (b) pretreatment is performed in a continuous mode. In other embodiments, the step (b) pretreatment is performed in a batch mode.

In some embodiments, the enzymatic hydrolysis of step (e) is performed in a continuous mode. In other embodiments, the enzymatic hydrolysis of step (e) is performed in a batch mode.

As will be readily understood by one of skill in the art, in both Process 1 and Process 2, the pH of compositions to undergo enzymatic hydrolysis or fermentation is typically adjusted to appropriate hydrolysis or fermentation pH levels, for example, to a pH as recited herein for hydrolysis or fermentation steps, to provide suitable conditions for the hydrolysis or fermentation.

In some embodiments, the lignocellulosic biomass is derived from softwoods. Achieving a high yield of saccharification products is more difficult to obtain from softwood-derived lignocellulosic biomass than from hardwood-derived lignocellulosic biomass. The processes described herein can provide high-yields of 1) cellulose-derived fermentable glucose and 2) hemicellulose-derived fermentable monomeric sugars from softwood-derived lignocellulosic biomass simultaneously in an economical manner without producing sticky lignin precipitates, wherein the combined yields are greater than about 80% based on available polysaccharides in the biomass. This yield is equivalent to greater than 585 BD kg per BD metric tonne of softwood biomass.

Surprisingly, pulp with high cellulose content and low residual lignin and hemicelluloses can be produced by using a pretreatment composition comprising only sulfur dioxide and water at relatively low temperatures (125-140° C.) without the use of a base (calcium, magnesium, sodium, ammonium, etc.) or organic solvent (alcohols, ketones, esters, etc.). The high cellulose content pulp can have a cellulose content of higher than 75%, higher than 80%, higher than 85%, or higher than 90%, based on weight of the dry pulp. The low residual lignin in the pulp can be a lignin content of less than 15%, less than 12%, or less than 9% lignin (weight %) based on the weight of the dry pulp. The low residual hemicelluloses in the pulp can be a hemicellulose content of less than 6%, less than 5%, or less than 4%, based on the weight of the dry pulp).

The pulp produced by the processes has very high enzymatic digestibility with over 85%, over 90%, or over 95%, glucan-to-glucose conversion at low enzyme dosage, such as 18 FPU per g glucan or less, or 9 FPU per g glucan or less. The sugars are readily fermentable to ethanol without detoxification, which may be due to the low sugar and lignin degradation in the process.

The processes utilize inexpensive sulfur dioxide that can be mostly recovered in a chemical recovery unit after pretreatment by simple depressurization. The recovery is almost complete, except for the small portion being bound to lignin in the form of lignosulfonic acids.

Surprising is also the fact that the pretreatment with high $SO_2$ concentration in the present disclosure (from 15 to 60%, based on total sulfur dioxide and water weight) performs considerably better than pretreatment with $SO_2$ concentrations of 3, 6 and even 10% (same basis, see Examples 1 and 2). The overall benefits of high $SO_2$ concentrations are surprising and have not been reported so far for sugar and/or ethanol production.

Surprisingly also despite relatively high sulfur dioxide charges, the sugar degradation is very low, and the combined sugar degradation products account for less than 0.3% based on BD biomass feed. This is lower than observed in other $SO_2$-based processes including sulfite, SPORL, and low $SO_2$ processes.

Surprising also is the fact that some biomass species, including pine wood, which is not suitable for acid sulfite pulping, can be utilized in the presently disclosed process without any problems. This may be explained by absence of hydrogen sulfite anions, which are speculated to initiate liquor or pretreatment composition decomposition in the presence of certain extractives (for example, pine heartwood containing pinosylvin cannot be delignified in sulfite pulping of pine).

Surprising also is the fact that, despite high $SO_2$ concentration and thus high acidity, lignin precipitation is not observed, and all lignin that is removed from fiber is present in water-soluble, mostly sulfonated, form. Thus, the sticky lignin precipitation problem is avoided in the processes described herein, which is a major benefit for continuous industrial operations.

Surprising also is the fact that the dissolved hemicelluloses are converted in the pretreatment process to monomeric sugars at about 90% or higher, and no further saccharification of hemicelluloses is required. This is surprising because in conventional sulfite pulping, some sugars are bound to sulfur dioxide in a form of alpha-hydroxysulfonic acids (loosely-bound $SO_2$) and sugar sulfonic acids.

Surprising also is that after pretreatment, the whole slurry without separation or detoxification can be enzymatically hydrolyzed at low enzyme charges with high yields of glucose and other sugars.

Surprising also is the fact that low temperature impregnation is not required for the presently disclosed process.

Furthermore, surprisingly the pretreatment does not require explosion of the fiber structure, contrary to the present state of the art. Thus, in addition to using centrifuges, cellulose washing is also possible using conventional industrial pulp and paper equipment, such as a filter wash press.

FIGS. 1 and 2 present the process flow diagrams according to a first and a second embodiment (Process 1 or Process 2) of the invention, as described herein.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention described herein.

DETAILED DESCRIPTION

Figure 1:
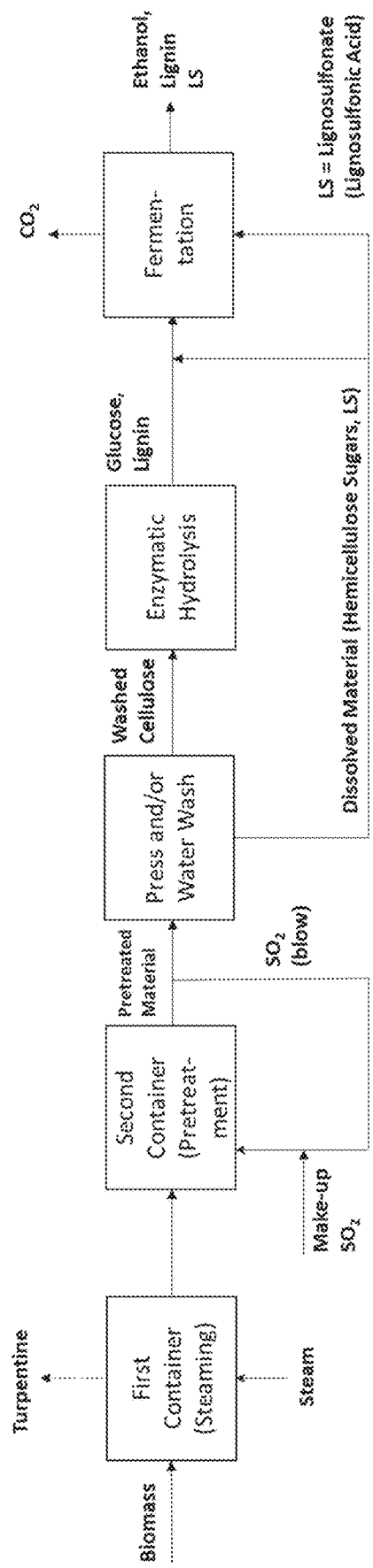
FIG. 1. A flowsheet example of the process for the production of cellulose, lignocellulosic sugars, lignosulfonate and ethanol, according to a first embodiment (Process 1).

The invention provides a process for the production of cellulose, lignocellulosic sugars, lignosulfonate, and ethanol, from lignocellulosic biomass. The process comprises steaming, pretreatment, chemical recovery, saccharification, and optionally fermentation. The pretreatment conditions use only sulfur dioxide and water, simultaneously resulting in high glucan conversion to glucose at low enzyme charges, high recovery of hemicellulose-derived monomeric sugars, and high lignosulfonate yield combined with the absence of lignin precipitates. High-yield production of ethanol through fermentation can be obtained using this process.

High glucan conversion to glucose is defined as higher than 85%, or higher than 90%. High recovery of hemicellulose-derived monomeric sugars is defined as higher 80%, higher than 85% or higher than 90%, theoretical monosaccharides yield from hemicellulose based on the amount of hemicellulose found in the lignocellulosic biomass fed into the process. High lignosulfonate yield is defined as higher than 75%, higher than 80%, higher than 85%, or higher than 90%. The absence of lignin precipitates is defined as gravimetric yield of precipitated material at less than 0.15% based on BD biomass, as obtained by centrifugation of the pretreatment liquor (liquid obtained by pressing solid fraction, after pretreatment of lignocellulosic biomass and sulfur dioxide removal) in a centrifuge at 8,000 RPM for 15 minutes. High-yield production of ethanol can be defined as higher than 83%, higher than 85%, higher than 87%, higher than 89%, or higher than 91%, based on theoretical 0.51 g ethanol per g monosaccharide.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The term "about" can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, composition, or embodiment. The term about can also modify the endpoints of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to bring about a recited effect, such as an amount necessary to form products in a reaction mixture. Determination of an effective amount is typically within the capacity of persons skilled in the art, especially in light of the detailed disclosure provided herein. The term "effective amount" is intended to include an amount of a compound or reagent described herein, or an amount of a combination of compounds or reagents described herein, e.g., that is effective to form products in a reaction mixture. Thus, an "effective amount" generally means an amount that provides the desired effect.

The term "substantially" is typically well understood by those of skill in the art and can refer to an exact ratio or configuration, or a ratio or configuration that is in the proximity of an exact value such that the properties of any variation are inconsequentially different than those ratios and configurations having the exact value. The term "substantially" may include variation as defined for the terms "about" and "approximately", as defined herein above.

The phrase "filter paper unit" or "FPU" refers to the measurement of cellulase activity using International Union of Pure and Applied Chemistry (IUPAC) guidelines (see Adney et al., Measurement of Cellulase Activities, Laboratory Analytical Procedure, Technical Report NREL/TP-510-42628, National Renewable Energy Laboratory, January 2008) and measures cellulase activity in terms of "filter-paper units" (FPU) per milliliter of original (undiluted) enzyme solution. The value of 2.0 mg of reducing sugar as glucose from 50 mg of filter paper (4% conversion) in 60 minutes has been designated as the intercept for calculating filter paper cellulase units (FPU) by IUPAC.

The yield of monosaccharides obtained from the processes described herein (e.g., as illustrated by FIGS. 4-7) take into account that approximately 10% of the weight of a monosaccharide is hydration water that was not present when the moiety was in polymerized form (e.g., as cellulose in wood) (about 10% in the case of hexose sugars (glucose, galactose, and mannose) and about 12% in the case of pentose sugars (xylose and arabinose)). The added weight of the isolated monosaccharide averages roughly 10.5% for softwoods. For example, the yield of monosaccharides obtained by the process illustrated in FIG. 5 for 18 FPU per g glucan is calculated as follows: 649 kg (total mono sugars produced for fermentation) (100-10.5)/100/653 kg (starting sugar equivalents from 1 metric tonne biomass)=89% yield.

It should be noted that when reported as %, the terms "conversion", "yield" and "recovery" are understood as synonymous, showing the obtained quantity of monosaccharides as % theoretical from original polysaccharides, or the obtained amount of lignosulfonate as % theoretical from original lignin.

Bleaching refers to the process of removing lignin from a composition or decolorizing lignin. Bleaching is typically carried out in one or more steps (e.g., 1-3) by applying various bleaching chemicals in each step, which either remove lignin or decolorize lignin. Suitable bleaching chemicals include, but are not limited to, oxygen in alkali (so-called 'oxygen delignification', or O-stage), chlorine dioxide (D-stage), hydrogen peroxide in alkali (P-stage), ozone (Z-stage), alkali extraction (E-stage), and enzymatic bleaching. Bleaching is a common and well-known practice used in bleached pulp production (for paper, tissue, etc.) and in dissolving pulp production.

Embodiments of the Invention

A process for the production of cellulose, lignocellulosic sugars, lignosulfonate, and ethanol is described herein. Steps of various embodiments of the process are as follows.

A steaming bin is charged with lignocellulosic biomass in the form of chips, fragments, forest residues, sawdust, or the like. The biomass is steamed to remove air, to saturate the biomass with water and to optionally remove and recover turpentine.

The biomass is impregnated and pretreated in a pressurized vessel with chemicals comprising sulfur dioxide and water, according to a recipe described herein.

After pretreatment, excess sulfur dioxide is released from the pretreated material at elevated temperature. Water vapor and other condensable gases are condensed, and the sulfur dioxide gas is optionally purified by removing traces of other compounds including but not limited to water vapor and other volatiles. Sulfur dioxide is then liquefied by pressure change and/or temperature reduction of the gas, providing liquid sulfur dioxide. Liquid sulfur dioxide is then reintroduced into the pretreatment vessel, optionally by pumping.

Decompression can be either sudden, i.e. explosive, to disrupt the fiber structure, or non-explosive, i.e., using a mild blow similar to the conventional blow practiced in traditional pulping, because cellulose digestibility by enzymes is surprisingly high in the latter case.

In one embodiment, the cellulose pulp is optionally pressed to remove excess liquor, and/or washed with water, to remove at least a portion of dissolved material comprising dissolved lignosulfonic acid, hemicellulose saccharides, sugars, and optionally dissolved lignin. Liquid removal and washing can be done, for example, by using centrifuges, a conventional filter press, or other conventional pulp mill equipment. In another embodiment, the slurry after pretreatment is neither pressed nor washed.

Pressed and/or washed cellulose pulp or the whole slurry after pretreatment is hydrolyzed to glucose using cellulolytic enzymes comprising cellulases, glucosidases, optionally hemicellulases, or mixtures thereof.

Cellulosic and hemicellulosic sugar streams can be combined, and after appropriate neutralization, fermented to ethanol and carbon dioxide. Separate usage of cellulosic and hemicellulosic streams is also envisioned. Cellulose-based glucose can be used as a source for chemical or biochemical transformation to value-added products. Cellulose can be used for preparation of nanocellulose and/or dissolving pulp, for example, viscose, cellulose ethers, and cellulose esters.

Lignosulfonate can be separated at any point after pretreatment, for example, after pulp washing, after enzymatic hydrolysis, after fermentation, or later during downstream processing. Lignosulfonate separation can be done, for example, by overliming, membrane filtration, or another suitable method. Alternatively, lignosulfonate and other processing residues can be partly or wholly combusted in a boiler or other equipment to produce heat and to optionally recover the sulfur dioxide bound to lignosulfonate.

The pretreatment conditions are given in Table 1 below.

TABLE 1

Pretreatment conditions.

| Parameter | Unit | Range |
| --- | --- | --- |
| Sulfur Dioxide Charge | weight % based on total sulfur dioxide and water | 15-60 |
| Water Charge | weight % based on total sulfur dioxide and water | 40-85 |
| Ratio of combined weight of SO$_2$ and water to BD weight of biomass | kg sulfur dioxide and water per kg BD biomass | 1-10 |
| Temperature | ° C. | 125-140 |
| Duration | min | 20-120 |

The disclosed pretreatment conditions result in production of high yields of cellulose or cellulose-derived fermentable glucose with simultaneously achieved high yields of fermentable hemicellulose-derived sugars and lignosulfonate, and absence of lignin precipitates. Polysaccharides conversion to monomeric sugars is higher than 82% or higher than 86% or higher than 90% or, for softwoods, the monosaccharides yield is higher than 600, higher than 620 or higher than 640 BD kg per BD tonne biomass. Optionally cellulose is obtained at about 400 BD kg per BD tonne biomass and hemicellulosic fermentable sugars are obtained at higher than 200, higher than 220, or higher than 240 BD kg per BD tonne softwood biomass. Lignin conversion to lignosulfonate is higher than 75%, higher than 80%, higher than 85% or higher than 90%. The absolute yields depend on the original composition of lignocellulosic biomass.

In another aspect, the first embodiment (Process 1) can be carried out as illustrated in FIG. 1 and as follows. Ethanol is produced from lignocellulosic biomass by a process comprising:

(a) contacting lignocellulosic biomass in a first container with steam, wherein the lignocellulosic biomass absorbs water from the steam, and air and optionally turpentine are removed from the lignocellulosic biomass;

(b) transferring the lignocellulosic biomass from the first container to a pressurized and heated second container and contacting the lignocellulosic biomass in the second container with a pretreatment composition comprising sulfur dioxide and water to impregnate the lignocellulosic biomass, optionally transferring the resulting impregnated lignocellulosic biomass to a third container or retaining in the second container for digestion, wherein the impregnated lignocellulosic biomass is heated under pressure for 20-120 minutes, and wherein the temperature in the heated container is from about 125° C. to about 140° C.;

wherein the pretreatment composition comprises 40-85 wt. % water and 15-60 wt. % sulfur dioxide based on the combined weight of water and sulfur dioxide, and the ratio of pretreatment composition to lignocellulosic biomass, based on dry weight of the lignocellulosic biomass, is about 1:1 to about 10:1;

thereby releasing and/or dissolving lignin and hemicellulose from the lignocellulosic biomass into the pretreatment composition, thereby producing a solid fraction comprising primarily cellulose from the lignocellulosic biomass;

wherein 75-100% of the lignin from the lignocellulosic biomass is sulfonated to produce lignosulfonic acid (LS), and at least about 80% or at least about 85% of the sugar moieties of the hemicellulose from the lignocellulosic biomass are hydrolyzed to monosaccharide form;

(c) releasing pressure from the pretreated material, and recovering sulfur dioxide from gas released from the pretreated material as a result of releasing pressure, and optionally retaining the material at elevated temperature to facilitate sulfur dioxide recovery;

(d) removing dissolved material from the cellulose by washing with water or by applying pressure to the cellulose to drain off the dissolved material, to provide washed cellulose, wherein the dissolved material is a first fermentable composition comprising lignosulfonic acid (LS), hemicellulose oligomers, and monosaccharides;

(e) contacting the washed cellulose with a cellulase, a glucosidase, a hemicellulase, or a combination thereof, to produce glucose referred to as glucose fraction, thereby forming a second fermentable composition, in combination with releasing a small amount of lignin from the washed cellulose, wherein a cellulase, a glucosidase, a hemicellulase, or a combination thereof are optionally added in a first reactor to achieve liquefaction, and the mixture is transferred to second reactor without addition of a cellulase, a glucosidase, a hemicellulase, or a combination thereof, to finalize hydrolysis;

(f) optionally adjusting the pH of the first fermentable composition, the second fermentable composition, or a combination of the first and second fermentable compositions, to provide a third, fourth, or fifth fermentable composition; and (g) subjecting one or more of the fermentable compositions to fermentation with yeast to produce ethanol.

Figure 2:
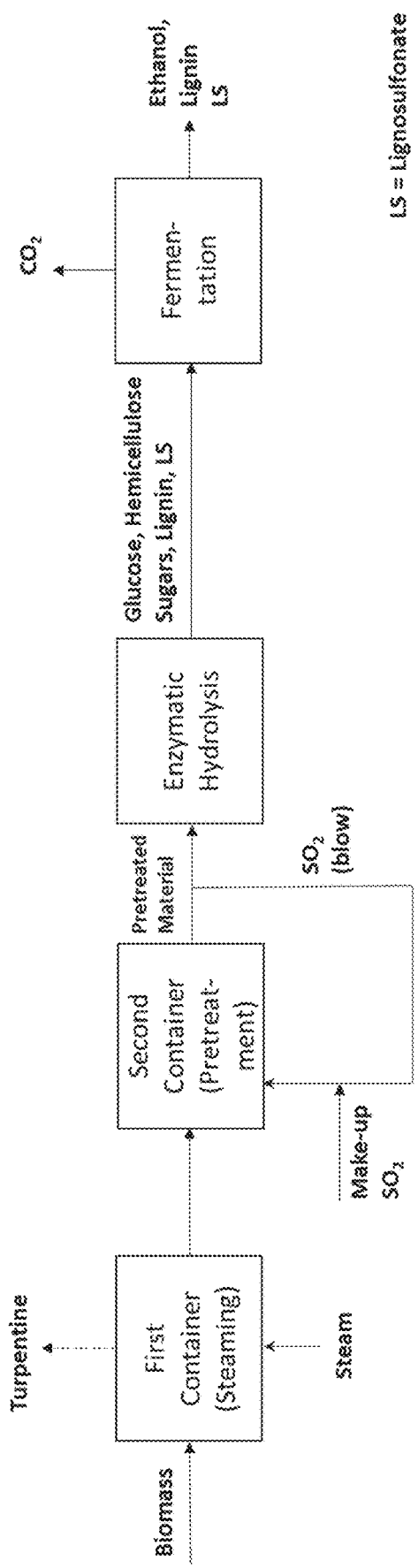
FIG. 2. A flowsheet example of the process for the production of lignocellulosic sugars, lignosulfonate and ethanol, according to a second embodiment (Process 2).

In another aspect, the second embodiment (Process 2) can be carried out as illustrated in FIG. 2 and as follows. Ethanol is produced from lignocellulosic biomass by a process comprising:

(a) contacting lignocellulosic biomass in a first container with steam, wherein the lignocellulosic biomass absorbs water from the steam, and air and optionally turpentine are removed from the lignocellulosic biomass;

(b) transferring the lignocellulosic biomass from the first container to a pressurized and heated second container and contacting the lignocellulosic biomass in the second container with a pretreatment composition comprising sulfur dioxide and water to impregnate the lignocellulosic biomass, optionally transferring the resulting impregnated lignocellulosic biomass to a third container or retaining in the second container for digestion wherein the impregnated lignocellulosic biomass is heated under pressure for 20-120 minutes, and wherein the temperature in the heated container is from about 125° C. to about 140° C.;

wherein the pretreatment composition comprises 40-85 wt. % water and 15-60 wt. % sulfur dioxide, and the ratio of pretreatment composition to dry lignocellulosic biomass, based on dry weight of the lignocellulosic biomass, is about 1:1 to about 10:1;

thereby releasing and/or dissolving lignin and hemicellulose from the lignocellulosic biomass into the pretreatment composition, thereby producing a solid fraction comprising primarily cellulose from the lignocellulosic biomass to provide a digested mixture;

wherein 75-100% of the lignin from the lignocellulosic biomass is sulfonated to produce lignosulfonic acid (LS), and at least about 80% or at least about 85% of the sugar moieties of the hemicellulose from the lignocellulosic biomass are hydrolyzed to monosaccharide form;

(c) releasing pressure from the pretreated material, and recovering sulfur dioxide from gas released from the pretreated material as a result of releasing pressure, and optionally retaining the material at elevated temperature to facilitate sulfur dioxide recovery;

(d) transferring the digested mixture to a container for enzymatic hydrolysis;

(e) adjusting the pH of digested mixture to a pH level suitable for enzymatic hydrolysis;

(f) contacting the pH-adjusted digested mixture in the container for enzymatic hydrolysis with a cellulase, a glucosidase, a hemicellulase, or a combination thereof, to provide a second mixture comprising glucose derived from cellulose, monosaccharides derived from hemicellulose, oligosaccharides, lignosulfonate salts of lignosulfonic acid, and lignin, wherein a cellulase, a glucosidase, a hemicellulase, or a combination thereof are optionally added in a first reactor to achieve liquefaction, and the mixture is transferred to second reactor without addition of a cellulase, a glucosidase, a hemicellulase, or a combination thereof, to finalize hydrolysis; and (g) subjecting the second mixture to fermentation with yeast to produce ethanol.

In some embodiments, the pretreatment composition comprises 40-80 wt. % water and 20-60 wt. % sulfur dioxide. In other embodiments, the pretreatment composition comprises 40-75 wt. % water and 25-60 wt. % sulfur dioxide. In yet further embodiments, the pretreatment composition comprises 40-70 wt. % water and 30-60 wt. % sulfur dioxide.

In some embodiments, the ratio of pretreatment composition to dry weight of lignocellulosic biomass is about 2:1 to about 8:1. In other embodiments, the ratio of pretreatment composition to dry lignocellulosic biomass is about 2.5:1 to about 6.5:1. In yet further embodiments, the ratio of pretreatment composition to dry lignocellulosic biomass is about 3:1 to about 4.5:1.

When pressure is released from the pretreated material, the pretreated material can optionally be maintained at an elevated temperature (e.g., about 60 to 140° C., about 60 to 80° C., about 80 to 100° C., about 100 to 120° C., or about 120 to 140° C.) to facilitate sulfur dioxide recovery.

Suitable pretreatment (digester) conditions according to Process 1 or Process 2 are summarized in the table below.

| Parameter | Unit | Value (±5%-20%) |
|---|---|---|
| Sulfur Dioxide Charge | weight % based on total sulfur dioxide and water | 40 |
| Sulfur Dioxide Charge | % on BD biomass | 160 |
| Ratio of combined weight of $SO_2$ and water to BD weight of biomass | kg sulfur dioxide and water per kg BD biomass | 4 |
| Temperature | ° C. | 135 |
| Duration | min | 45-90 |

In some embodiments, the step (b) pretreatment is performed in a continuous mode. In other embodiments, the step (b) pretreatment is performed in a batch mode. In a continuous mode, the biomass and the pretreatment chemicals, i.e. sulfur dioxide and water, are continuously fed to the second container and the pretreatment products and unreacted chemicals are continuously removed from the second container, while the second container is maintained at a substantially constant pressure and temperature. In a batch mode, the biomass and the pretreatment chemicals are fed to the second container, followed by heating the container and retaining biomass with the pretreatment chemicals for a desired time in the second container, and subsequent discharge of the pretreatment products and unreacted chemicals.

In some embodiments, the enzymatic hydrolysis is performed in a continuous mode. A neutralized cellulose slurry and the enzymes can be continuously fed into a liquefaction reactor and the liquefied slurry is continuously removed from the liquefaction reactor and continuously fed into a hydrolysis reactor. When Process 1 is performed in a continuous mode, the glucose produced in step (e) is continuously removed from the hydrolysis reactor. When Process 2 is performed in a continuous mode, the mixture of glucose, monosaccharides, oligosaccharides, lignosulfonate salts, and lignin produced in step (e) ('the second mixture') is continuously removed from the hydrolysis reactor. Alternatively, the neutralized cellulose slurry and the enzymes are continuously fed into a hydrolysis reactor, and glucose is continuously removed from the hydrolysis reactor in Process 1 or the mixture of glucose, monosaccharides, oligosaccharides, lignosulfonate salts, and lignin is continuously removed from the hydrolysis reactor in Process 2. The liquefaction and hydrolysis reactors are typically maintained at constant pH, temperature, and mixing rate.

In other embodiments, the enzymatic hydrolysis is performed in a batch mode. For example, the neutralized cellulose slurry and the enzymes are fed into a hydrolysis reactor, followed by retaining the material at desired temperature, pH, mixing rate and time, followed by discharging the glucose fraction or the mixture of glucose, monosaccharides, oligosaccharides, lignosulfonate salts, and lignin from the hydrolysis reactor.

In various embodiments, the process further comprising bleaching the solid fraction comprising mainly cellulose obtained in step (b), referred to as the washed pulp, to produce bleached cellulose that can be converted to dissolving pulp, including but not limited to viscose, cellulose ethers, and cellulose esters.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. High Sulfur Dioxide Pretreatment

Scots pine sawdust (biomass) containing 54.4% moisture (as-received basis), 43.9% glucan (oven dry basis), 5.2% xylan, 3.4% galactan, 2.0% arabinan, 10.9% mannan, 1.4% acetyl groups, 27.2% lignin, 1.0% acetone extractives and 0.1% ash was pretreated in rotating mini-reactors submerged in heated oil. The pretreatment composition comprising sulfur dioxide and water were charged such that the moisture-adjusted sulfur dioxide concentration was 40 weight % (for high $SO_2$ experiments) and from 3 to 10 weight % (for low $SO_2$ experiments). The water concentration was from 60 to 97 weight %, based on total weight of sulfur dioxide and water (including water from sawdust). The combined weight of sulfur dioxide and water was 4 kg per 1 kg of dry biomass. Note that even though 10% $SO_2$ pretreatment is not generally falling into the category of low $SO_2$ pretreatments, it is placed there due to similar performance.

Pretreatment temperature was between 130 and 165° C., heating up time to final temperature was about 15 min, time at final temperature was from 60 to 120 min, cooling down time was about 2 minutes (cooling by submerging the mini-reactors in ice water). Unreacted sulfur dioxide was removed slowly from the system by venting, and no fiber explosion was used. Cellulosic pulp was separated from the spent liquor (using nylon bag) and washed thrice with water.

The results of high $SO_2$ and low $SO_2$ pretreatment experiments are given in Table 2. It can be observed that in the low $SO_2$ process, the obtained pulps are very dark and have very high residual lignin content (38-52%). Thus, the low $SO_2$ pretreatment suffers from high lignin condensation and lignin reprecipitation on the fibers which is termed a 'black cook' in sulfite pulping practice. On the other hand, in the high $SO_2$ pretreatment experiments, the pulps are mostly light brown and contain a small amount of residual lignin (about 12-14% for pulps H-1, H-2 and H-3 and 15.6% for pulp H-4). Compositional analysis of pulps shows high cellulose content (for example, about 82% for H-1 and about 85% for H-3). Sugar degradation is surprisingly low, despite high $SO_2$ concentration, as evidenced by the low concentration of combined sugar degradation products (furfural, hydroxymethylfurfural and levulinic acid) level at less than 0.3%, based on original BD biomass. Total saccharides recovery after pretreatment is surprisingly high. For example, for H-1, the value is over 95%, and for H-3 it is over 96% of available polysaccharides in biomass. In the low $SO_2$ pretreatment experiments, the saccharides recovery after pretreatment is between 77 and 93%.

TABLE 2

Pretreatment streams yields and composition.

| | Pretreatment type | | | | | | |
|---|---|---|---|---|---|---|---|
| | High SO$_2$ | | | | Low SO$_2$ | | |
| Pretreatment conditions set No. | H-1 | H-2 | H-3 | H-4 | L-1 | L-2 | L-3 |
| Sulfur dioxide concentration, weight % based on total sulfur dioxide and water | 40 | 40 | 40 | 40 | 3.0 | 7.0 | 10 |
| Pretreatment temperature, ° C. | 135 | 130 | 130 | 130 | 165 | 155 | 145 |
| Pretreatment duration, min | 60 | 60 | 90 | 120 | 60 | 60 | 60 |
| Cellulosic Pulp | | | | | | | |
| Pulp color | Light Brown | Light Brown | Light Brown | Brown | Black | Very dark brown | Dark brown |
| Cellulosic pulp yield, % on o.d. biomass | 47.0 | 46.0 | 47.5 | 46.3 | 56.2 | 59.3 | 61.3 |
| Glucan in pulp, % on pulp | 82.3 | 78.4 | 84.7 | 73.9 | 45.5 | 54.7 | 61.0 |
| Hemicelluloses in pulp, % on o.d. pulp | 5.7 | 5.7 | 5.5 | 3.3 | 3.8 | 2.3 | 3.4 |
| Acetyl groups in pulp, % on o.d. pulp | 0.0 | 0.0 | 0.0 | 0.0 | 0.0 | 0.0 | 0.0 |
| Lignin in pulp, % on o.d. pulp | 12.1 | 13.6 | 13.4 | 15.6 | 52.2 | 44.9 | 37.8 |
| Kappa number of pulps | 46 | 54 | 51 | 54 | 175 | 135 | 100 |
| Dissolved Saccharides | | | | | | | |
| Monomeric sugars (as anhydro), % on o.d. biomass | 18.9 | 18.6 | 17.0 | 18.8 | 20.2 | 18.7 | 18.9 |
| Oligomeric sugars (as anhydro), % on o.d. biomass | 2.1 | 2.8 | 3.0 | 2.5 | 2.3 | 1.9 | 2.4 |
| Total Saccharides Recovery | | | | | | | |
| Total saccharides recovery from biomass, % | 95.4 | 91.9 | 96.2 | 87.4 | 77.0 | 83.4 | 93.1 |
| Sugar Degradation Products | | | | | | | |
| Furfural, % on o.d. biomass | 0.1 | 0.0 | 0.0 | 0.0 | 0.1 | 0.0 | 0.0 |
| Hydroxymethylfurfural, % on o.d. biomass | 0.0 | 0.0 | 0.0 | 0.0 | 0.0 | 0.0 | 0.0 |
| Levulinic acid, % on o.d. biomass | 0.2 | 0.0 | 0.1 | 0.2 | 2.1 | 0.9 | 0.3 | o.d.—oven dried.

Example 2. Enzymatic Digestibility and Fermentability of High SO$_2$ Pretreatment Streams The washed cellulosic pulps obtained in Example 1 from high SO$_2$ and low SO$_2$ pretreatments (pretreatment conditions set Nos. H-1 and L-3) were subjected to enzymatic hydrolysis in shake flasks, in duplicate. A commercially available enzyme cocktail containing cellulases, hemicellulases and β-glucosidases was used at charges of 5.4, 9.0 and 18 FPU per g glucan in pulp. Total solids content during enzymatic hydrolysis was 9%, pH was maintained at 4.8-5.3 using an ammonium hydroxide solution, and temperature was 54° C. The shaking rate was 250 RPM during liquefaction (first hour) and 150 RPM during the rest of hydrolysis.

Figure 3:
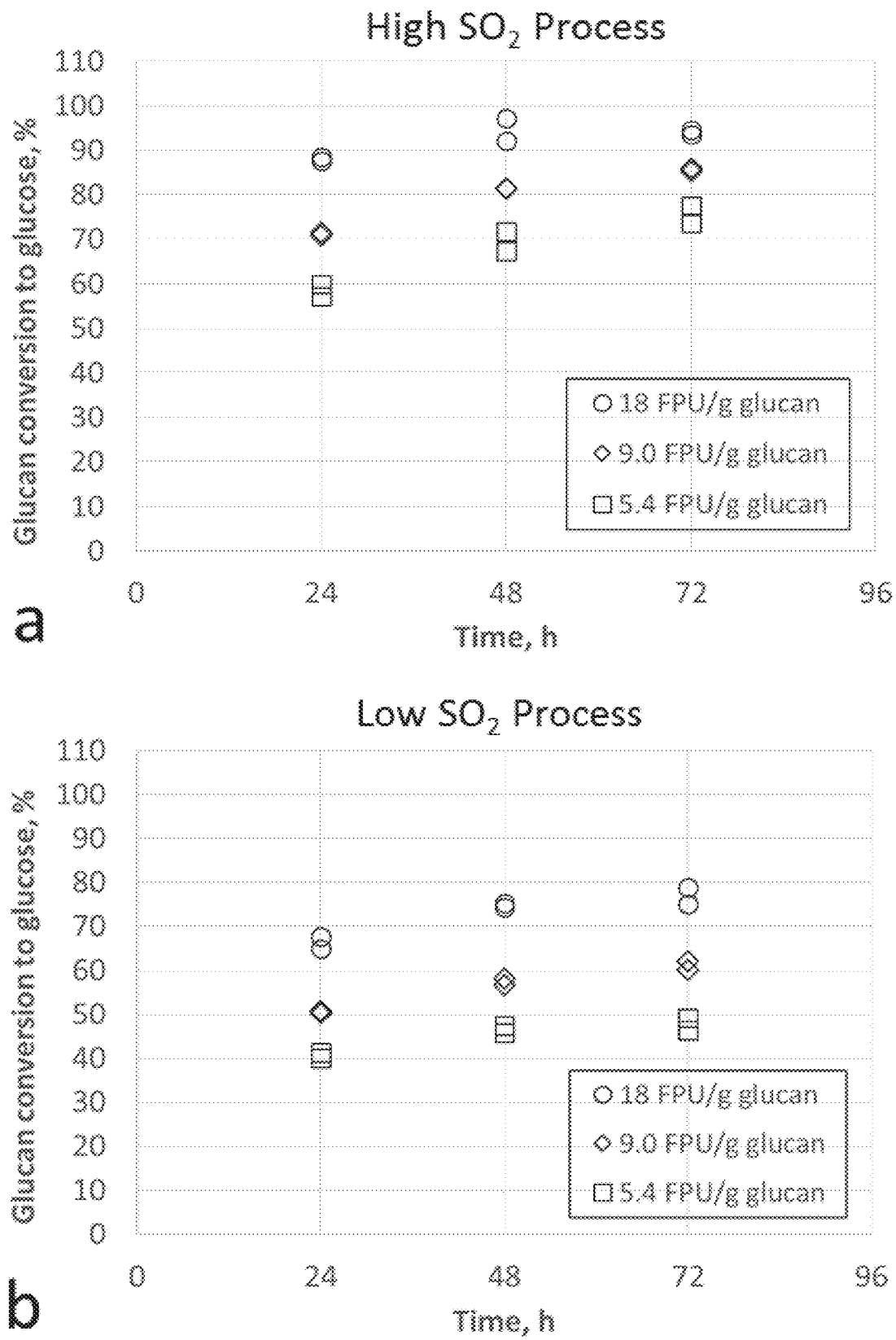
FIG. 3. Enzymatic digestibility of cellulosic pulp obtained using the described high $SO_2$ process H-1 in Example 2 (a and c), in comparison with low $SO_2$ process L-3 in Example 2 (b and c), and total monomeric sugar yield in enzymatic hydrolysis of the whole slurry after high $SO_2$ process in Example 3 (d), at 7 FPU/BD g wood. FPU—filter paper unit, a measure of enzyme charge; TS—total solids.
Figure 3:
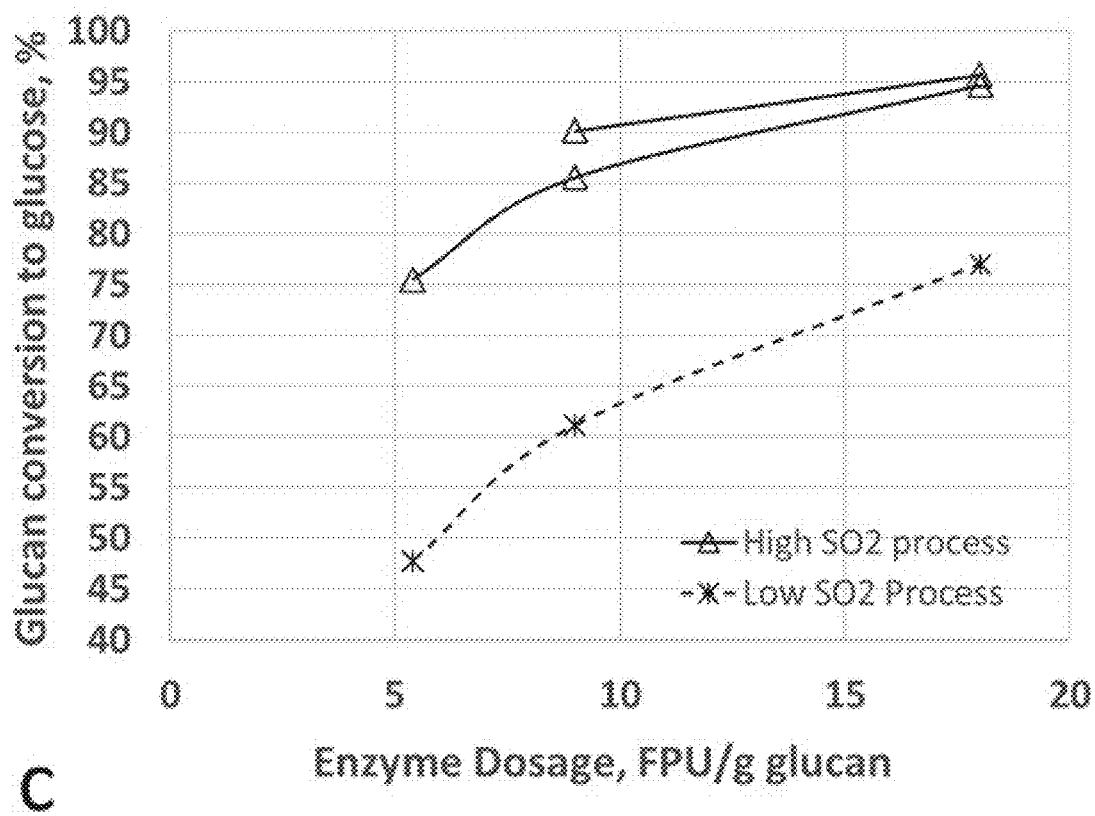
Figure 3:
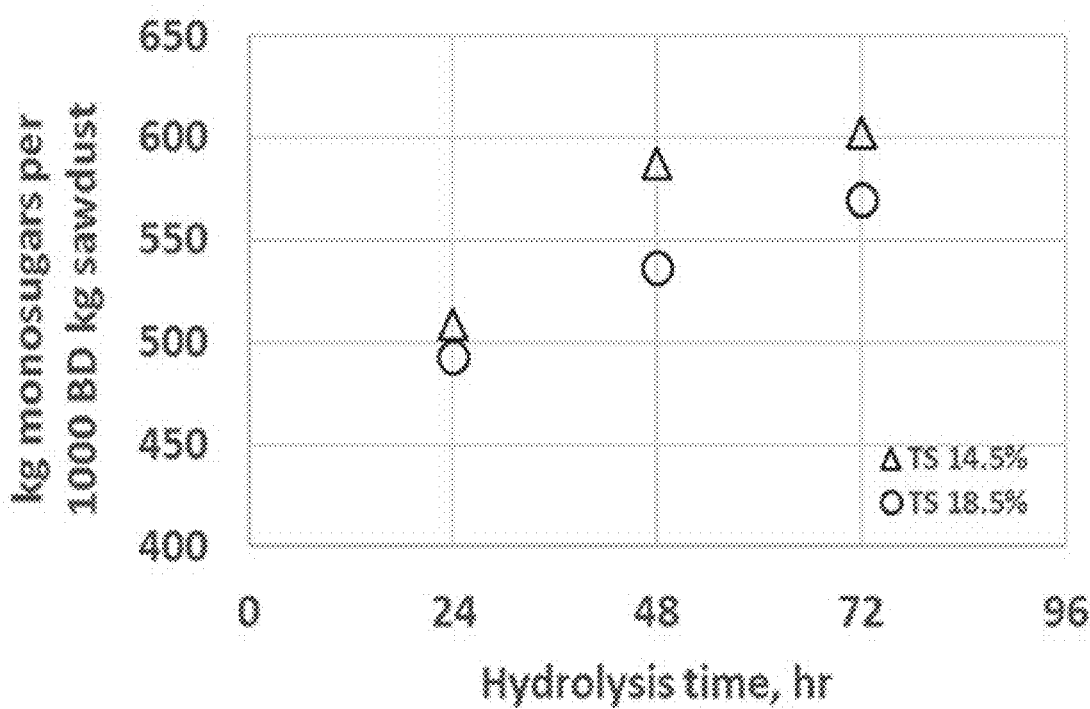
Figure 4:
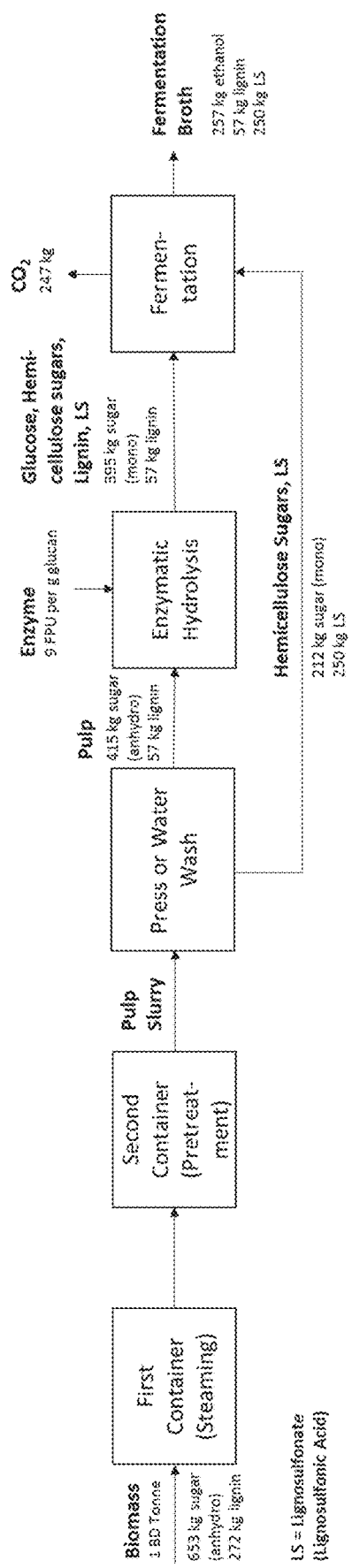
FIG. 4. Example of a process flow diagram, according to Process 1, with product yields based on 1 tonne of dry biomass using 9 FPU per gram glucan. Calculations show that over 83% of available saccharides in the original biomass are converted to monosaccharides.
Figure 5:
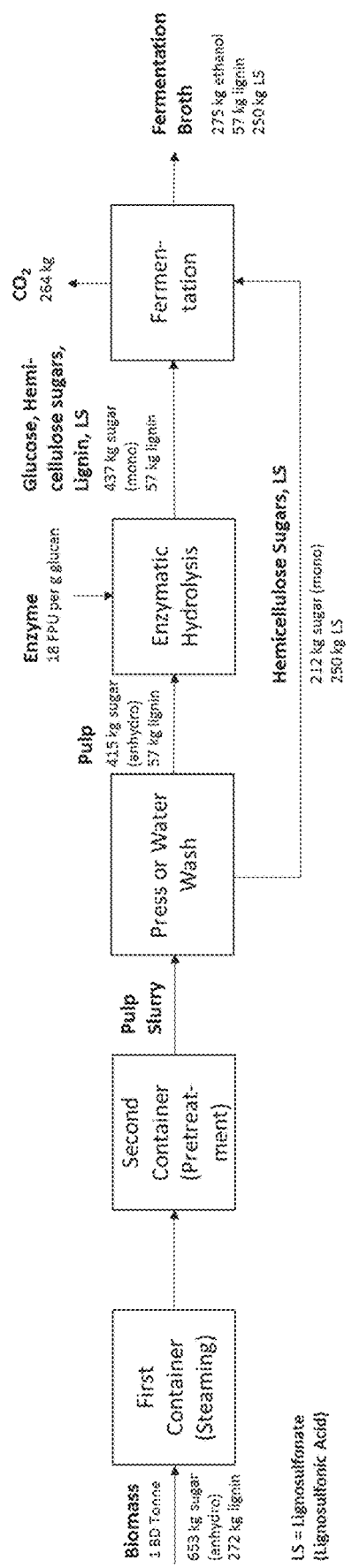
FIG. 5. Example of a process flow diagram, according to Process 1, with product yields based on 1 tonne of dry biomass using 18 FPU per gram glucan. Calculations show that over 89% of available saccharides in the original biomass are converted to monosaccharides.
Figure 6:
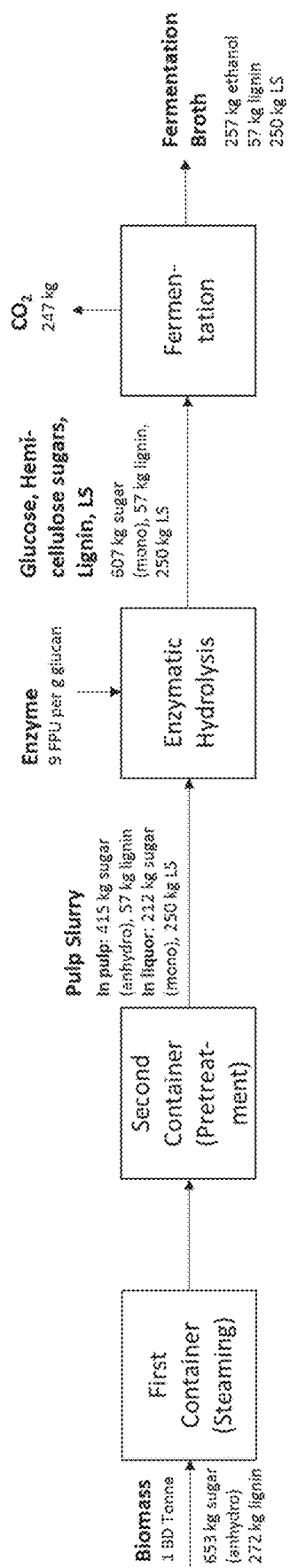
FIG. 6. Example of a process flow diagram, according to Process 2, with product yields based on 1 tonne of dry biomass using 9 FPU per gram glucan. Calculations show that over 83% of available saccharides in the original biomass are converted to monosaccharides.
Figure 7:
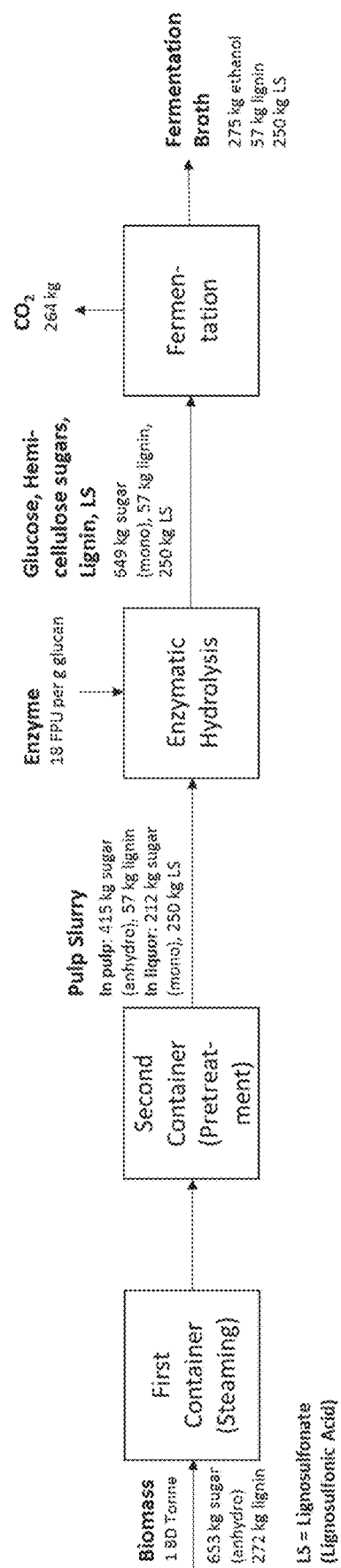
FIG. 7. Example of a process flow diagram, according to Process 2, with product yields based on 1 tonne of dry biomass using 18 FPU per gram glucan. Calculations show that over 89% of available saccharides in the original biomass are converted to monosaccharides.

FIG. 3 shows that the cellulosic pulp obtained in high SO$_2$ pretreatment (H-1) is highly digestible by enzymes with about 85% glucan-to-glucose conversion achieved already at enzyme charge of 9.0 FPU/g glucan and 72 h, even though no fiber explosion was used. At an enzyme charge of 18 FPU/g glucan, the 72-hour conversion reached about 95%. Considerably lower glucan-to-glucose conversions were obtained for the low SO$_2$ pretreatment experiments: about 60% at enzyme charge of 9.0 FPU/g glucan and about 77% at enzyme charge of 18 FPU/g glucan, all values at 72 h. The much lower residual lignin content of the high SO$_2$ pulp is likely responsible for the much better enzymatic conversion rates. The enzymatic hydrolysates obtained are termed glucose sugar streams.

A portion of the pretreatment liquors (liquid obtained by pressing solid fraction, after pretreatment of lignocellulosic biomass and sulfur dioxide removal) obtained from example 1 (pretreatment conditions set Nos. H-1 and L-3) were centrifuged at 8,000 RPM and 15 min, and the precipitate was quantified as 0.0% and 0.6% on o.d. biomass for H-1 and L-3 liquors, respectively. This suggests higher effectiveness of sulfonation and dissolution of lignin at high SO$_2$ pretreatment vs. low SO$_2$ pretreatment. Absence of lignin precipitates is of high importance for equipment availability.

Glucose sugar streams from the H-1 and L-3 experiments were mixed with the corresponding pretreatment liquors in proportions corresponding to the sugars amounts in original biomass. The mixtures were neutralized to pH 5.8-6.0 and fermented in shake flasks (150 RPM) at pH=5.0-5.8, in duplicate, by a commercially available genetically modified yeast strain, capable of utilizing all five wood sugars. Suitable examples of yeast cells and fermentation techniques are described in US Patent Publication No. 2019/0106464 (Oeser et al.). The process can optionally employ a combination of yeast strains capable of utilizing all five wood sugars. The initial sugar concentration was 65-75 g/L, inoculation was done with 0.5 g/L yeast. Temperature was 32° C. Fermentation took less 24 hours where over 98% of sugars were consumed. For the H-1 experiment, the ethanol yield was at least 83.1% of theoretical or higher, i.e. 0.42 g ethanol/g sugar or higher. For the L-3 experiment, the ethanol yield was at least 78.6% of theoretical or higher, i.e. 0.40 g ethanol/g sugar. Higher fermentation yield in the case of high SO$_2$ pretreatment may be explained by lower concentration of fermentation inhibitors.

Examples of process flow diagrams and the product yields are depicted in FIGS. 4-7.

Example 3. Enzymatic Digestibility of the Mixed Slurry from High SO$_2$ Pretreatment Scots pine sawdust (biomass) containing 54.4% moisture (as-received basis), 43.9% glucan (oven dry basis), 5.2% xylan, 3.4% galactan, 2.0% arabinan, 10.9% mannan, 1.4% acetyl groups, 27.2% lignin, 1.0% acetone extractives and 0.1% ash was pretreated in rotating minireactors submerged in heated oil. Sulfur dioxide and water were charged such that the moisture-adjusted sulfur dioxide concentration was 40 weight % and water concentration was from 60 weight %, based on total weight of sulfur dioxide and water (including water from sawdust). The combined weight of sulfur dioxide and water was 4 kg per 1 kg of dry biomass.

Pretreatment temperature was 135° C., heating up time to final temperature was about 15 min, time at final temperature was 60 min, cooling down time was about 2 minutes (cooling by submerging the mini-reactors in ice water). Unreacted sulfur dioxide was removed slowly from the system by venting, and no fiber explosion was used. No separation of pulp and liquor took place. The whole slurry was subjected to enzymatic hydrolysis in shake flasks. A commercially available enzyme cocktail containing cellulases, hemicellulases and β-glucosidases was used at a charge of 7 FPU per BD g wood.

Total solids content during enzymatic hydrolysis was 14.5 and 18.5%, pH was maintained at 5.0-5.5 using an ammonium hydroxide solution, and temperature was 54° C. The shaking rate was 250 RPM during the first five hours and 150 RPM during the rest of hydrolysis.

The 72-hour wood glucan conversion to glucose was about 88 and 80% at total solids 14.5 and 18.5%, respectively. The 72-hour total wood polysaccharides conversion to monomeric sugars was about 83 and 78% at total solids 14.5 and 18.5%, respectively. This translates into 602 and 570 kg monomeric sugar yield per BD tonne pine sawdust, respectively (FIG. 3d).

REFERENCES CITED: PATENT DOCUMENTS

1. EP 2376642 (Sjoede) "LIGNOCELLULOSIC BIOMASS CONVERSION BY SULFITE PRETREATMENT"
2. EP 2516660 (Van Der Meulen) "PRE-TREATMENT OF CELLULOSIC MATERIAL"
3. U.S. Pat. No. 8,038,842 (Retsina) "METHOD FOR VAPOR PHASE PULPING WITH ALCOHOL, SULFUR DIOXIDE AND AMMONIA"
4. U.S. Pat. No. 8,268,125 (Retsina) "METHOD FOR VAPOR PHASE PULPING WITH ALCOHOL AND SULFUR DIOXIDE"
5. U.S. Pat. No. 8,834,633 (Van Der Meulen) "PRE-TREATMENT OF CELLULOSIC MATERIAL"
6. U.S. Pat. No. 9,528,129 (Van Der Meulen) "PRE-TREATMENT OF CELLULOSIC MATERIAL"
7. U.S. Pat. No. 9,574,212 (Foody) "PROCESS COMPRISING SULFUR DIOXIDE AND/OR SULFUROUS ACID PRETREATMENT AND ENZYMATIC HYDROLYSIS"
8. U.S. Pat. No. 10,421,667 (Foody) "PROCESS FOR TREATING LIGNOCELLULOSIC FEEDSTOCK COMPRISING WET OXIDATION"

REFERENCES CITED: OTHER PUBLICATIONS

1. Achyuthan, K. E., Achyuthan, A. M., Adams, P. D., Dirk, S. M., Harper, J. C., Simmons, B. A., Singh A. K. (2010) Supramolecular self-assembled chaos: polyphenolic lignin's barrier to cost effective lignocellulosic biofuels. Molecules 15, 8641-8688.
2. Ewanick, S. M., Bura, R., Saddler, J. N. (2007) Acid-Catalyzed Steam Pretreatment of Lodgepole Pine and Subsequent Enzymatic Hydrolysis and Fermentation to Ethanol. Biotechnol. Bioeng. 98, 737-746.
3. Galbe, M., Zacchi, G. (2002) A review of the production of ethanol from softwood. Appl. Microbiol. Biotechnol. 59, 618-628.
4. Gutsch, J. S., Sixta, H. Holzforschung 2011, 65, 511-518.
5. Kumar, L., Arantes, V., Chandra, R., Saddler, J. The lignin present in steam pretreated softwood binds enzymes and limits cellulose accessibility. Bioresource Technology 2012, 103, 201-208.
6. Morales, L. O., Iakovlev, M., Martin-Sampedro, R., Rahikainen, J., Laine, J., van Heiningen, A., Rojas, O. Effects of residual lignin and heteropolysaccharides on the bioconversion of softwood lignocellulose nanofibrils obtained by SO$_2$-Ethanol-Water (SEW) fractionation. Bioresource technology 2014, 161, 55-62.
7. Nakagame, S.; Chandra, R. P.; Saddler, J. N. (2010) The effect of isolated lignins, obtained from a range of pretreated lignocellulosic substrates, on enzymatic hydrolysis. Biotechnol. Bioeng. 2010, 105, 871-879.
8. Pérez, J. A., Gonzalez, A., Oliva, J. M., Ballesteros, I., Manzanares, P. (2007) Effect of process variables on liquid hot water pretreatment of wheat straw for bioconversion to fuel-ethanol in a batch reactor. Journal of Chemical Technology and Biotechnology 82, 929-938.
9. Pfister, K., Sjostrom, E. (1977) The formation of monosaccharides and aldonic and uronic acids during sulfite cooking Paperi ja Puu 59(11), 711-712, 715-716, 719-720.
10. Rahikainen, J., Mikander, S., Marjamaa, K., Tamminen, T., Lappas, A., Viikari, L., Kruus, K. Inhibition of enzymatic hydrolysis by residual lignins from softwood—study of enzyme binding and inactivation on lignin-rich surface. Biotechnol Bioeng 2011, 108, 2823-2834.
11. Sixta, H., Potthast, A., Krotschek, A. W. (2006) Chemical pulping processes, in Handbook of Pulp, Vol. 1, Sixta, H., Eds. WILEY-VCH, Weinheim, 109-509.
12. Sjöström, E. (1981) Wood chemistry. Fundamentals and applications. Academic Press, Inc., San Diego.
13. Soderstrom, J., Galbe, M., Zacchi, G. (2004) Effects of washing on yield in one- and two-step steam pretreatment of softwood for production of ethanol. Biotechnology Progress 20, 744-749.
14. Stanciu, C., Ciurea, A. (2008) Research concerning formation, characterization and recovery of lignin polymeric deposits in order to get some lignin-phenol-formaldehyde resins. Mater. Plast. 45, 232-235.
15. Stenberg, K., Tengborg, C., Galbe, M., Zacchi, G. (1998) Optimisation of Steam Pretreatment of SO2-Impregnated Mixed Softwoods for Ethanol Production. J. Chem. Technol. Biotechnol. 71, 299-308.
16. S. Tian, W. Zhu, R. Gleisner, X. J. Pan, J. Y. Zhu (2011) Comparisons of SPORL and dilute acid pretreatments for sugar and ethanol productions from aspen. Biotechnol. Prog. 27, 419-427.

17. Varnai, A., Siika-aho, M., Viikari, L. Restriction of the enzymatic hydrolysis of steam-pretreated spruce by lignin and hemicellulose. Enzyme Microb. Technol. 2010, 46, 185-193.
18. Z. J. Wang, J. Y. Zhu, Ronald S. Zalesny, K. F. Chen (2012) Ethanol production from poplar wood through enzymatic saccharification and fermentation by dilute acid and SPORL pretreatments. Fuel 95, 606-614.
19. Yamamoto, M, Iakovlev, M., van Heiningen, A. The effect of chemical and physical characteristics of spruce SEW pulps on enzymatic hydrolysis. Cellulose 2014, 21, 3395-3407.
20. Yu, Z., Jameel, H., Chang, H., Park, S. (2011) The effect of delignification of forest biomass on enzymatic hydrolysis. Bioresour Technol 102, 9083-9089.
21. Zhu, J. Y., Zhu, W., O'Bryan, P., Dien, B. S., Tian, S., Gleisner, R., Pan, X. J. (2010) Appl. Microbiol. Biotechnol. 86, 1355-1365.
22. Zhu, J. Y., Chandra, M. S., Gu, F., Gleisner, R., Reiner, R., Sessions, J., Marrs, G., Gao, J., Anderson, D. (2015) Using sulfite chemistry for robust bioconversion of Douglas-fir forest residue to bioethanol at high titer and lignosulfonate: A pilot-scale evaluation. Bioresource Technology 2015, 179, 390-397.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A process for producing cellulose, lignocellulosic sugars, lignosulfonate, and ethanol, from lignocellulosic biomass comprising:
   (a) contacting lignocellulosic biomass in a first container with steam, wherein the lignocellulosic biomass absorbs water from the steam, thereby removing air from the lignocellulosic biomass;
   (b) contacting the steamed lignocellulosic biomass in a second container with a pretreatment composition comprising sulfur dioxide and water at a temperature between 125° C. and 133° C. under pressure for 20-90 minutes to generate pretreated material;
   wherein the pretreatment composition comprises about 40 wt. % sulfur dioxide and about 60 wt. % water based on the combined weight of sulfur dioxide and water (including water from the steamed lignocellulosic biomass), and the ratio of pretreatment composition to lignocellulosic biomass dry weight is from about 1 to 8 kg/kg (including water from the steamed lignocellulosic biomass in the mass of the pretreatment composition);
   thereby releasing and/or dissolving lignin and hemicellulose from the lignocellulosic biomass into the pretreatment composition and leaving a solid fraction comprising cellulose, wherein the lignin content in the solid fraction comprising cellulose is less than 14 wt. %, the cellulose yield is about 87 wt. % to about 97 wt. % based on the amount of cellulose in the lignocellulosic biomass, and a total saccharide recovery from the lignocellulosic biomass after steps (a) and (b) is greater than 91%;
   wherein 75-100% of the lignin from the lignocellulosic biomass is sulfonated to produce lignosulfonic acid (LS), and at least about 85% of the sugar moieties of the released hemicellulose from the lignocellulosic biomass are hydrolyzed to monosaccharide form; and
   wherein the pretreated material comprises 0.1 wt. % furfural or less; 0.2 wt. % levulinic acid or less, and less than 0.1 wt. % hydroxymethylfurfural, with respect to dry weight of the pretreated material;
   (c) releasing pressure from the pretreated material, and recovering sulfur dioxide from gas released from the pretreated material as a result of releasing pressure;
   (d) removing dissolved material from the cellulose by washing with water or by applying pressure to the cellulose to drain off the dissolved material, to provide washed cellulose or pressed cellulose, referred to as a washed cellulose stream, wherein the dissolved material comprises lignosulfonic acid (LS), lignin, hemicellulose oligomers, and monosaccharides;
   (e) adjusting the pH of the washed cellulose stream from step (d) and contacting it with a cellulase, a glucosidase, a hemicellulase, or a combination thereof, to produce glucose and to release small amounts of insoluble lignin and hemicellulose-derived monosaccharides; and
   (f) neutralizing the glucose and the dissolved material to an appropriate pH level and subjecting the glucose, the dissolved material, or a combination thereof to fermentation to produce ethanol.

2. The process of claim 1 wherein recovering sulfur dioxide comprises:
   (i) releasing gas comprising sulfur dioxide and water vapor from the pretreated material at elevated temperature and optionally lower pressure;
   (ii) condensing the gas to provide a gas comprising sulfur dioxide and a liquid comprising water;
   (iii) liquefying the gas comprising sulfur dioxide by pressure change and/or temperature reduction to provide liquid sulfur dioxide; and
   (iv) introducing the liquid sulfur dioxide to a container for contacting steamed lignocellulosic biomass with a pretreatment composition.

3. The process of claim 2 wherein the gas comprising sulfur dioxide is purified by removing water vapor and organic volatiles.

4. The process of claim 2 wherein the liquid sulfur dioxide is stored as liquid sulfur dioxide in a separate container before being reused in the pretreatment composition in step (b) of the process.

5. The process of claim 1 wherein the pretreated material after step (c) and/or the dissolved material after step (d) is retained at elevated temperature, to facilitate sulfur dioxide recovery.

6. The process of claim 1 where the step (b) pretreatment is performed in a continuous mode.

7. The process of claim 1 where the step (b) pretreatment is performed in a batch mode.

8. The process of claim 1 where the enzymatic hydrolysis of step (e) is performed in a continuous mode.

9. The process of claim 1 where the enzymatic hydrolysis of step (e) is performed in a batch mode.

10. The process of claim 1 wherein one or more of water, phosphoric acid, hydrochloric acid, sulfuric acid, nitric acid, acetic acid, formic acid, oxalic acid, and process condensates are added to step (c), step (d), or both.

11. The process of claim 1 wherein washed cellulose stream, the dissolved material, the glucose, or a combination thereof, are subjected to pH adjustment to a pH of 7-11, before enzyme hydrolysis step (e), before fermentation step (f), or before both steps (e) and (f), followed by pH adjustment to a pH of less than 7.

12. The process of claim 1 wherein residual sulfur dioxide is removed from the washed cellulose stream, from the dissolved material, from the glucose, or from a combination thereof, before enzyme hydrolysis step (e), before fermentation step (f), or before both steps (e) and (f), by adding one or more aqueous solutions comprising formaldehyde, acetaldehyde, or hydrogen peroxide.

13. The process of claim 1 further comprising bleaching the washed pulp to produce cellulose that can be converted to nanocellulose and/or dissolving pulp, including but not limited to viscose, cellulose ethers, and cellulose esters.

14. The process of claim 1 wherein the process produces at least about 257 kg of ethanol and at least about 250 kg lignosulfonate per bone dry tonne of wood sawdust.

15. A process for producing lignocellulosic sugars, lignosulfonate, and ethanol, from lignocellulosic biomass comprising:
(a) contacting lignocellulosic biomass in a first container with steam, wherein the lignocellulosic biomass absorbs water from the steam, thereby removing air from the lignocellulosic biomass;
(b) contacting the steamed lignocellulosic biomass in a second container with a pretreatment composition comprising sulfur dioxide and water at a temperature between 125° C. and 133° C. under pressure for 20-90 minutes to generate pretreated material;
wherein the pretreatment composition comprises about 40 wt. % sulfur dioxide and about 60 wt. % water based on the combined weight of sulfur dioxide and water (including water from the steamed lignocellulosic biomass), and the ratio of pretreatment composition to lignocellulosic biomass dry weight is from about 1 to 8 kg/kg (including water from the steamed lignocellulosic biomass in the mass of the pretreatment composition);
thereby releasing and/or dissolving lignin and hemicellulose from the lignocellulosic biomass into the pretreatment composition and leaving a solid fraction comprising cellulose, wherein the lignin content in the solid fraction comprising cellulose is less than 14 wt. %, the cellulose yield is about 87 wt. % to about 97 wt. % based on the amount of cellulose in the lignocellulosic biomass, and a total saccharide recovery from the lignocellulosic biomass after steps (a) and (b) is greater than 91%;
wherein 75-100% of the lignin from the lignocellulosic biomass is sulfonated to produce lignosulfonic acid (LS), and at least about 85% of the sugar moieties of the released hemicellulose from the lignocellulosic biomass are hydrolyzed to monosaccharide form; and
wherein the pretreated material comprises 0.1 wt. % furfural or less; 0.2 wt. % levulinic acid or less, and less than 0.1 wt. % hydroxymethylfurfural, with respect to dry weight of the pretreated material;
(c) releasing pressure from the pretreated material and recovering sulfur dioxide from gas released from the pretreated material as a result of releasing pressure, producing a first mixture;
(d) neutralizing the first mixture to an appropriate pH level for enzymatic hydrolysis;
(e) contacting the neutralized first mixture with a cellulase, a glucosidase, a hemicellulase, or a combination thereof, to provide a second mixture comprising glucose derived from cellulose and monosaccharides derived from hemicellulose as well as lignosulfonate (salt of lignosulfonic acid), lignin, and oligosaccharides; and
(f) adjusting pH of the second mixture and subjecting the second mixture to fermentation to produce ethanol.

16. The process of claim 15 wherein recovering sulfur dioxide comprises:
(i) releasing gas comprising sulfur dioxide and water vapor from the pretreated material at elevated temperature and optionally lower pressure;
(ii) condensing the gas to provide a gas comprising sulfur dioxide and a liquid comprising water;
(iii) liquefying the gas comprising sulfur dioxide by pressure change and/or temperature reduction to provide liquid sulfur dioxide; and
(iv) introducing the liquid sulfur dioxide to a container for contacting steamed lignocellulosic biomass with a pretreatment composition.

17. The process of claim 16 wherein the gas comprising sulfur dioxide is purified by removing traces of water vapor and organic volatiles.

18. The process of claim 16 wherein the liquid sulfur dioxide is stored as liquid sulfur dioxide in a separate container before being reused in the pretreatment composition in step (b) of the process.

19. The process of claim 15 wherein the pretreated material is retained at elevated temperature after step (c), to facilitate sulfur dioxide recovery.

20. The process of claim 15 wherein one or more of water, phosphoric acid, hydrochloric acid, sulfuric acid, nitric acid, acetic acid, formic acid, oxalic acid, and process condensates are added to step (c).

21. The process of claim 15 wherein the first mixture after step (c), the second mixture after step (e), or both, are subjected to pH adjustment to a pH of 7-11, before enzyme hydrolysis step (e), before fermentation step (f), or before both steps (e) and (f), followed by pH adjustment to a pH of less than 7.

22. The process of claim 15 wherein residual sulfur dioxide is removed from the first mixture after step (c), from the second mixture after step (e), or from both, by adding one or more aqueous solutions comprising formaldehyde, acetaldehyde, or hydrogen peroxide.

23. The process of claim 15 wherein the process produces at least about 257 kg of ethanol and at least about 250 kg lignosulfonate per bone dry tonne of wood sawdust.

24. A process for producing cellulose, lignocellulosic sugars, lignosulfonate, and ethanol, from wood sawdust comprising:
(a) contacting wood sawdust in a first container with steam, wherein the wood sawdust absorbs water from the steam, thereby removing air from the wood sawdust;
(b) contacting the steamed wood sawdust in a second container with a pretreatment composition comprising sulfur dioxide and water at a temperature of about 130° C. under pressure for about 60-90 minutes to generate pretreated material;

wherein the pretreatment composition comprises about 40 wt. % sulfur dioxide and about 60 wt. % water based on the combined weight of sulfur dioxide and water (including water from the steamed wood sawdust), and the ratio of pretreatment composition to wood sawdust dry weight is from about 2 kg/kg to 8 kg/kg (including water from the steamed wood sawdust in the mass of the pretreatment composition);

thereby releasing and/or dissolving lignin and hemicellulose from the wood sawdust into the pretreatment composition and leaving a solid fraction comprising cellulose, wherein the lignin content in the solid fraction comprising cellulose is less than 14 wt. %, the cellulose yield is about 87 wt. % to about 97 wt. % based on the amount of cellulose in the wood sawdust, and a total saccharide recovery from the wood sawdust after steps (a) and (b) is greater than 91%;

wherein at least about 85% of the lignin from the wood sawdust is sulfonated to produce lignosulfonic acid (LS), and at least about 85% of the sugar moieties of the released hemicellulose from the wood sawdust are hydrolyzed to monosaccharide form; and wherein the pretreated material comprises less than 0.1 wt. % furfural; less than 0.1 wt. % hydroxymethylfurfural, and about 0.1 wt. % levulinic acid or less, with respect to dry weight of the pretreated material;

(c) releasing pressure from the pretreated material, and recovering sulfur dioxide from gas released from the pretreated material as a result of releasing pressure;

(d) removing dissolved material from the cellulose by washing with water or by applying pressure to the cellulose to drain off the dissolved material, to provide washed cellulose or pressed cellulose, referred to as a washed cellulose stream, wherein the dissolved material comprises lignosulfonic acid (LS), lignin, hemicellulose oligomers, and monosaccharides;

(e) adjusting the pH of the washed cellulose stream from step (d) and contacting it with a cellulase, a glucosidase, a hemicellulase, or a combination thereof, to produce glucose and to release small amounts of insoluble lignin and hemicellulose-derived monosaccharides; and (f) neutralizing the glucose and the dissolved material to an appropriate pH level and subjecting the glucose, the dissolved material, or a combination thereof to fermentation to produce ethanol, wherein when the glucose and dissolved material are subjected to fermentation, at least about 275 kg ethanol per bone dry tonne of wood sawdust is produced.

25. A process for producing ethanol and lignosulfonate from wood sawdust comprising:

(a) contacting wood sawdust in a first container with steam, wherein the wood sawdust absorbs water from the steam, thereby removing air from the wood sawdust;

(b) contacting the steamed wood sawdust in a second container with a pretreatment composition comprising sulfur dioxide and water at a temperature of about 130° C. under pressure for about 60-90 minutes to generate pretreated material;

wherein the pretreatment composition comprises about 40 wt. % sulfur dioxide and 60 wt. % water based on the combined weight of sulfur dioxide and water (including water from the steamed wood sawdust), and the ratio of pretreatment composition to wood sawdust dry weight is from about 2 kg/kg to 8 kg/kg (including water from the steamed wood sawdust in the mass of the pretreatment composition);

thereby releasing and/or dissolving lignin and hemicellulose from the wood sawdust into the pretreatment composition and leaving a solid fraction comprising cellulose, wherein the lignin content in the solid fraction comprising cellulose is less than 14 wt. %, the cellulose yield is about 87 wt. % to about 97 wt. % based on the amount of cellulose in the wood sawdust, and a total saccharide recovery from the wood sawdust after steps (a) and (b) is greater than 91%; and wherein the pretreated material comprises 0.1 wt. % furfural or less; 0.2 wt. % levulinic acid or less, and less than 0.1 wt. % hydroxymethylfurfural, with respect to dry weight of the pretreated material;

wherein at least 85% of the lignin from the wood sawdust is sulfonated to produce lignosulfonic acid (LS), and at least about 85% of the sugar moieties of the released hemicellulose from the wood sawdust are hydrolyzed to monosaccharide form;

(c) releasing pressure from the pretreated material and recovering sulfur dioxide from gas released from the pretreated material as a result of releasing pressure, producing a first mixture;

(d) neutralizing the first mixture to an appropriate pH level for enzymatic hydrolysis;

(e) contacting the neutralized first mixture with a cellulase, a glucosidase, a hemicellulase, or a combination thereof, to provide a second mixture comprising glucose derived from cellulose and monosaccharides derived from hemicellulose as well as lignosulfonate (salt of lignosulfonic acid), lignin, and oligosaccharides; and (f) adjusting pH of the second mixture and subjecting the second mixture to fermentation to produce at least about 275 kg of ethanol per bone dry tonne of wood sawdust.

* * * * *